(12) United States Patent
Baudner et al.

(10) Patent No.: US 9,827,190 B2
(45) Date of Patent: Nov. 28, 2017

(54) INTRADERMAL DELIVERY OF IMMUNOLOGICAL COMPOSITIONS COMPRISING TOLL-LIKE RECEPTOR 7 AGONISTS

(71) Applicants: Barbara Baudner, Siena (IT); Simona Gallorini, Siena (IT); Derek O'Hagan, Winchester, MA (US)

(72) Inventors: Barbara Baudner, Siena (IT); Simona Gallorini, Siena (IT); Derek O'Hagan, Winchester, MA (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 14/764,997

(22) PCT Filed: Jan. 30, 2014

(86) PCT No.: PCT/EP2014/051860
§ 371 (c)(1),
(2) Date: Jul. 31, 2015

(87) PCT Pub. No.: WO2014/118305
PCT Pub. Date: Aug. 7, 2014

(65) Prior Publication Data
US 2015/0366796 A1   Dec. 24, 2015

Related U.S. Application Data

(60) Provisional application No. 61/759,751, filed on Feb. 1, 2013.

(30) Foreign Application Priority Data

May 28, 2013   (EP) .................................. 13169596

(51) Int. Cl.
| | | |
|---|---|---|
| A61K 9/00 | (2006.01) | |
| A61K 39/39 | (2006.01) | |
| A61K 39/095 | (2006.01) | |
| A61K 39/145 | (2006.01) | |
| C12N 7/00 | (2006.01) | |
| A61K 39/00 | (2006.01) | |

(52) U.S. Cl.
CPC .......... *A61K 9/0021* (2013.01); *A61K 39/095* (2013.01); *A61K 39/145* (2013.01); *A61K 39/39* (2013.01); *C12N 7/00* (2013.01); *A61K 2039/545* (2013.01); *A61K 2039/55511* (2013.01); *A61K 2039/55544* (2013.01); *A61K 2039/55572* (2013.01); *A61K 2039/55583* (2013.01); *C12N 2760/16134* (2013.01); *C12N 2760/16171* (2013.01)

(58) Field of Classification Search
CPC .................. A61K 9/0021; A61K 39/39; A61K 2039/55511
USPC ........................................... 424/210.1, 250.1
See application file for complete search history.

(56) References Cited

U.S. PATENT DOCUMENTS

| | | |
|---|---|---|
| 4,057,685 A | 11/1977 | McIntyre |
| 4,356,170 A | 10/1982 | Jennings et al. |
| 4,459,286 A | 7/1984 | Hilleman et al. |
| 4,663,160 A | 5/1987 | Tsay et al. |
| 4,666,886 A | 5/1987 | Baschang et al. |
| 4,673,574 A | 6/1987 | Anderson |
| 4,695,624 A | 9/1987 | Marburg et al. |
| 4,761,283 A | 8/1988 | Anderson |
| 4,808,700 A | 2/1989 | Anderson et al. |
| 4,882,317 A | 11/1989 | Marburg et al. |
| 4,965,338 A | 10/1990 | Tabanicia et al. |
| 5,936,076 A | 8/1999 | Higa et al. |
| 6,699,703 B1 | 3/2004 | Doucette-Stamm et al. |
| 6,800,744 B1 | 10/2004 | Doucette-Stamm |
| 6,945,952 B2 | 9/2005 | Kwon |
| 7,182,747 B2 | 2/2007 | Kwon |
| 7,211,062 B2 | 5/2007 | Kwon |
| 112,509 A1 | 5/2011 | Nozaki et al. |
| 2005/0192248 A1 | 9/2005 | Tsuji et al. |
| 2005/0215517 A1 | 9/2005 | Rossignol et al. |
| 2009/0004222 A1* | 1/2009 | O'Hagan ............. A61K 39/145 424/206.1 |
| 2009/0182306 A1* | 7/2009 | Lee et al. ............. A61K 9/0021 604/506 |
| 2010/0143301 A1 | 6/2010 | Desai et al. |
| 2011/0053893 A1* | 3/2011 | Wu et al. ............. C07F 9/6561 514/81 |

FOREIGN PATENT DOCUMENTS

| | | |
|---|---|---|
| EP | A0208375 | 1/1987 |
| EP | A2289843 | 4/1988 |

(Continued)

OTHER PUBLICATIONS

Nina Bhardwaj et al.; title: TLR Agonists: Are They Good Adjuvants? Cancer J. 2010; 16(4): 382-391; available in PMC Jul. 1, 2011.*
Adamou et al., "DNA Immunization of mice with plasmid encoding Neisseria gonorrhea PorB protein by intramuscular injection and epidermal particle bombardment", Infect. Immun. 69(2):949-958 (2001).
Bal, et al., "Influence of Microneedle Shape on the Transport of a Fluorescent Dye Into Human Skin in vivo" J. Control. Release, 147:218-24 (2010).
Baldrick, et al., "Safety Evaluation of Monophosphoryl Lipid A (MNPL): An immunostimulatory Adjuvant", Regulatory Toxicol. Pharmacol., 35:398-413 (2002).
Baraldo, et al., "N19 Polyepitope as a Carrier for Enhanced Immunogenicity and Protective Efficacy of Meningococcal Conjugate Vaccines", Infect. Immun. 72(8):4884-7. (2004).
Bazin, et al., New synthesis of Glycolipid Immunostimulants RC-529 and CRX-524, Tetrahedron Lett., 47:2087-92 (2006).

(Continued)

Primary Examiner — Yanzhi Zhang
(74) Attorney, Agent, or Firm — Virginia G. Campen

(57) ABSTRACT

An intradermal delivery system comprises an immunogenic composition comprising a TLR agonist and immunogen and a microneedle. The immunogenic composition may comprise a solid biodegradable microneedle or a solid coated microneedle. The intradermal delivery system may be formulated into a skin patch.

5 Claims, 4 Drawing Sheets

(56) References Cited

FOREIGN PATENT DOCUMENTS

| | | |
|---|---|---|
| EP | A0372501 | 12/1989 |
| EP | A0378881 | 7/1990 |
| EP | A0427347 | 5/1991 |
| EP | A0594610 | 12/1991 |
| EP | A0471177 | 2/1992 |
| GB | A2220211 | 1/1990 |
| WO | WO91/01146 | 2/1991 |
| WO | WO93/13202 | 7/1993 |
| WO | WO93/17712 | 9/1993 |
| WO | WO94/03208 | 2/1994 |
| WO | WO95/17211 | 6/1995 |
| WO | WO97/37026 | 10/1997 |
| WO | WO97/43303 | 10/1997 |
| WO | WO98/18928 | 5/1998 |
| WO | WO98/18930 | 5/1998 |
| WO | WO98/18931 | 5/1998 |
| WO | WO98/58668 | 12/1998 |
| WO | WO99/24578 | 5/1999 |
| WO | WO99/36544 | 7/1999 |
| WO | WO99/27109 | 10/1999 |
| WO | WO99/53940 | 11/1999 |
| WO | WO99/57280 | 11/1999 |
| WO | WO99/58562 | 11/1999 |
| WO | WO00/06737 | 2/2000 |
| WO | WO00/06738 | 2/2000 |
| WO | WO00/12131 | 3/2000 |
| WO | WO00/12689 | 3/2000 |
| WO | WO00/10599 | 5/2000 |
| WO | WO00/33882 | 6/2000 |
| WO | WO00/37105 | 6/2000 |
| WO | WO00/37494 | 6/2000 |
| WO | WO00/56360 | 9/2000 |
| WO | WO00/58475 | 10/2000 |
| WO | WO00/61761 | 10/2000 |
| WO | WO00/76540 | 12/2000 |
| WO | WO01/12219 | 2/2001 |
| WO | WO01/70955 | 9/2001 |
| WO | WO01/72337 | 10/2001 |
| WO | WO01/81380 | 12/2001 |
| WO | WO02/08426 | 1/2002 |
| WO | WO02/18595 | 3/2002 |
| WO | WO02/22167 | 3/2002 |
| WO | WO02/22168 | 3/2002 |
| WO | WO02/34771 | 5/2002 |
| WO | WO02/34773 | 5/2002 |
| WO | WO02/059148 | 8/2002 |
| WO | WO02/079241 | 10/2002 |
| WO | WO02/079243 | 10/2002 |
| WO | WO 02/085442 | 10/2002 |
| WO | WO-02/085446 A2 | 10/2002 |
| WO | WO02/091998 | 11/2002 |
| WO | WO02/094851 | 11/2002 |
| WO | WO02/094868 | 11/2002 |
| WO | WO02/102829 | 12/2002 |
| WO | WO03/011223 | 2/2003 |
| WO | WO03/011899 | 2/2003 |
| WO | WO03/049762 | 6/2003 |
| WO | WO03/068811 | 8/2003 |
| WO | WO03/082183 | 10/2003 |
| WO | WO03/093306 | 11/2003 |
| WO | WO03/097091 | 11/2003 |
| WO | WO03/104272 | 12/2003 |
| WO | WO03/105769 | 12/2003 |
| WO | WO2004/041157 | 5/2004 |
| WO | WO2004/092209 | 10/2004 |
| WO | WO2005/002619 | 1/2005 |
| WO | WO2005/032582 | 4/2005 |
| WO | WO2005/079315 | 9/2005 |
| WO | WO2005/102049 | 11/2005 |
| WO | WO2006/032472 | 3/2006 |
| WO | WO2006/032475 | 3/2006 |
| WO | WO2006/032500 | 3/2006 |
| WO | WO2007/000343 | 1/2007 |
| WO | WO2007/030477 | 3/2007 |
| WO | WO2007/040840 | 4/2007 |
| WO | WO2007/053455 | 5/2007 |
| WO | WO2007/059289 | 5/2007 |
| WO | WO2007/061964 | 5/2007 |
| WO | WO2007/113222 | 10/2007 |
| WO | WO2007/113223 | 10/2007 |
| WO | WO2007/113224 | 10/2007 |
| WO | WO2007/116322 | 10/2007 |
| WO | WO2007/124393 | 11/2007 |
| WO | WO2007/127976 | 11/2007 |
| WO | WO2008/005555 | 1/2008 |
| WO | WO2008/019162 | 2/2008 |
| WO | WO2008/047174 | 4/2008 |
| WO | WO2008/047249 | 4/2008 |
| WO | WO2009/040548 | 4/2009 |
| WO | WO2009/067081 | 5/2009 |
| WO | WO2009/111337 | 9/2009 |
| WO | WO2009/118296 | 10/2009 |
| WO | WO2010/014913 | 2/2010 |
| WO | WO2011/049677 | 4/2011 |
| WO | WO2011/119759 | 9/2011 |
| WO | WO 2011/151723 | 12/2011 |
| WO | WO-2011/151723 A2 | 12/2011 |
| WO | WO2012/031140 | 3/2012 |

OTHER PUBLICATIONS

Bethe et al., "The Cell Wall-Associated Serine Protease PrtA: A Highly Conserved Virulence Factor of *Streptoccocus pneumoniae*", FEMS Microbiol. Lett. 205(1):99 (2001).

Bethell, et al., "A Novel Method of Activation of Cross-linked Agaroses with 1,1'-Carbonyldiimidazole Which Gives a Matrix for Affinity Chromatography Devoid of Additional Charged Groups", Biol. Chem., 254, 2572-4 (1979).

Briles et al., "Immunization of Humans With Recombinant Pneumococcal Surface Protein A (RPspA) Elicits Antibodies That Passively Protect Mice From Fatal Infection With *Streptococcus Pneumoniaw* Bearing Heterologuous PspA", J. Infect. Dis. 182:1694-1701 (2000).

Brown et al., "Immunization with Components of Two Iron Uptake ABC Transporters Protects Mice against Systemic *Streptococcus pneumoniae*", Infection Infect. Immun., 69:6702-6706 (2001).

Carey et al. "Microneedle Array Design Determines the Induction of Protective Memory CD8 T Cell Responses Induced by a Recombinant Live Malaria Vaccine in Mice", PLoS ONE, 6(7): e22442 (2011).

Cassone, et al., "Opportunistic Fungi and Fungal Infections: the Challenge of a Single, General Antifungal Vaccine" Expert Rev. Vaccines, 5:859-67 (2006).

Coler, et al., "Development and Characterization of Synthetic Glucopyranosyl Lipid Adjuvant System as a Vaccine Adjuvant" PLoS ONE, 6(1):e16333 (2011).

da Hora, et al., "Non-Toxic Derivatives of LT as potent adjuvants" Vaccine, 29:1538-44 (2011).

Dale, et al., "Recombinant, Octavalent Group A *Streptococcal* M Protein Vaccine", Vaccine 14(10): 944-948 (1996).

Dale, JB, "Multivalent Group A *Streptococcal* Vaccine Designed to Optimize the Immunogenicity of Six Tandem M Protein Fragments", Vaccine 17:193-200 (1999).

Davidson et al., "Transdermal drug delivery by coated microneedles: Geometry effects on effective skin thickness and drug permeability", Chemical Engineering Research and Design, 86:1196-1206 (2008).

De Libero et al, "Recognition of lipid antigens by T cells", Nature Reviews Immunology, 5: 485-496 (2005).

Donnelly, et al., "Design, Optimization and Characterisation of Polymeric Microneedle Arrays Prepared by a Novel Laser-Based Micromoulding Technique", Pharm. Res., 28:41-57 (2011).

Evans, et al., "Enhancement of Antigen-Specific Immunity via the TLR4 Ligands MPL™ adjuvant and Ribi.529", Expert Rev. Vaccines, 2:219-229 (2003).

Falugi, et al., "Rationally Designed Strings of Promiscuous CD4+ T Cell Epitopes Provide Help to Haemophilus Influenzae Type B Oligosaccharide: A Model for New Conjugate Vaccines", Eur. J Immunol., 31:3816-3824 (2001).

(56) References Cited

OTHER PUBLICATIONS

Feng, et al., "LT(K63/R72), a New Mutant of *Escherichia coli* Heat-labile Enterotoxin, Exhibits Characteristics More Similar to LT(K63) than LT(R72).", Acta Biochim. Biophys. Sin. (Shanghai), 37(2):126-32 (2005).
Gill, et al., "Coated microneedles for transdermal delivery", J. Control. Release, 117:227-37 (2007).
Wong, et al., "Safety, Pharmacokinetics, and Pharmacodynamics of E5564, A Lipid A Antagonist, During Ascending Single-Dose Clinical Study" J. Clin. Pharmacol., 43(7):735-42 (2003).
Yang, et al., "The C-Glycoside analogue of the immunostimulant α-Galactosylceramide (KRN7000): Synthesis and striking enhancement of activity", Angew. Chem. Int. Ed., 43: 3818-3822 (2004).
Zhu et al., "DNA Immunization of mice with a plasmid encoding *Neisseria gonorrhea* PorB protein by intramuscular injection and epidermal particle bombardment", Vaccine 22:660-669 (2004).
DeMuth, et al., "Engineered microneedle arrays for transcutaneous HIV vaccine delivery", Retrovirology, 9(Supp 2):P334 (2012).
Guo, et al., "Enhanced transcutaneous immunization via dissolving microneedle array loaded with liposome encapsulated antigen and adjuvant", International Journal of Pharmaceutics, 447(1-2):22-30 (2013).
Kis, et al., "Devices for intradermal vaccination", Vaccine, 30(3):523-538 (2012).
Pattani, et al., "Microneedle mediated intradermal delivery of adjuvanted recombinant HIV-1 CN54gp140 effectively primes mucosal boost inoculations", Journal of Controlled Release, 162(3):529-537 (2012).
Edelman (2002). "The development and use of vaccine adjuvants," Mol Biotechnol. 21(2):129-48.
Spickler et al. (2003). "Adjuvants in veterinary vaccines: modes of action and adverse effects," J Vet Intern Med. 17(3):273-81.
Weldon et al. (2012). "Effect of adjuvants on responses to skin immunization by microneedles coated with influenza subunit vaccine," PLoS One. 7(7):e41501.
Mitsui, H. et al. (2004). "Differential expression and function of Toll-like receptors in Langerhans cells: comparison with splenic dendritic cells," Journal of Investigative Dermatology, 122(1):95-102.
Suzuki, H. Et al. (2000). "Imiquimod, a Topical Immune Response Modifier, Induces Migration of Langerhans Cells," Journal of Investigative Dermatology, 114(1):135-141.
Giuliani, et al., A universal vaccine for serogroup B meningococcus Proc. Natl .Acad. Sci. USA,. 103:10834-9 (2006).
Goff, et al., "Effects of Lipid Chain Lengths in α-Galactosylceramides on Cytokine Release by Natural Killer T Cells", J. Am. Chem., Soc., 126: 13602-13603 (2004).
Hearn, et al..,"Application of 1,1-Carbonyldiimidazole-Activated Matrices for the Purification of Proteins", J. Chromatogr., 218, 509-18 (1981).
Hoskins et al., "Genome of the Bacterium *Streptococcus pneumoniae* Strain R6", J. Bacteriol. 183:5709-5717 (2001).
Jin, et al., "Mass Producible and Biocompatible Microneedle Patch and Functional Verification of its Usefulness for Transdermal Drug Delivery", Biomed. Microdevices, 11(6):1195-203 (2009).
Johnson, et al., "3-O-Desacyl Monophosphoryl Lipid A Derivatives: Synthesis and Immunostimulant Activities", J. Med. Chem., 42:4640-9 (1999).
Johnson, et al., "Synthesis and Biological Evaluation of a New Class of Vaccind Adjuvants: Aminoalkyl Glucosaminide 4-Phosphates (AGPs)", Bioorg. Med. Chem. Lett., 9:2273-2278 (1999).
Jomaa et al., "Immunization with the iron uptake ABC transporter proteins PiaA and PiuA prevents respiratory infection with *Streptococcus pneumoniae*" Vaccine 24(24):5133-5139 (2006).
Kang, et al., "Microneedle and mucosal delivery of influenza vaccines" Expert Rev. Vaccines, 11(5):547-60 (2012).
Keitel, et al., "Increasing Doses of Purified Influenza Virus Hemagglutinin and Subvirion Vaccines Enhance Antibody Responses in the Elderly", Clin. Diagn. Lab. Immunol. 3:507-10 (1996).

Koutsonanos, et al., "Delivery of Subunit Influenza Vaccine to Skin With Microneedles Improves Immunogenicity and Long-Lived Protection", Sci. Rep., 2:357 (2012).
Koutsonanos, et al., "Transdermal Influenza Immunization with Vaccine-Coated Microneedle Arrays", PLoS ONE, 4(e): e4773 (2009).
Kuo, et al., "Characterization of a Recombinant Pneumolysin and Its Use as a Protein Carrier for Pneumococcal Type 18C Conjugate Vaccines", Infect. Immun. 63:2706-13 (1995).
Lee, et al., "Dissolving Microneedles for Transdermal Drug Delivery", Biomaterials, 29(13):2113-24 (2008).
LeMieux et al., "Rrga and Rrgb Are Components of a Multisubunit Pilus Encoded by the *Streptococcus pneumoniae* RlrA Pathogenicity Islet", Infect. Imm. 74:2453-2456 (2006).
Matsuo, et al., "A low-invasive and effective transcutaneous immunization system using a novel dissolving microneedle array for soluble and particulate antigens", J. Control. Release, 161:10-17 (2012).
Matsuo, et al., "Transcutaneous immunization using a dissolving microneedle array protects against tetanus, diphtheria, malaria, and influenza" J. Control. Release, 160(3):495-501 (2012).
Michon, et al., "Multivalent Pneumococcal Capsular Polysaccharide Conjugate Vaccines Employing Genetically Detoxified Pneumolysin as a Carrier Protein", Vaccine, 16:1732-41 (1998).
Oh, et al. "Intradermal influenza vaccine delivery using skin-penetrating dissolvable vaccine microneedles", American Association of Pharmaceutical Scientists, 2006 Annual Meeting and Exposition. The AAPS Journal, 8(S2) (2006).
Oki, et al, "The Clinical Implication and Molecular Mechanism of Preferential IL-4 Production by Modified Glycolipids-Stimulated NKT Cells", J. Clin. Investig., 113: 1631-1640.
Peppoloni, et al., "Mutants of the *Escherichia coli* Heat-Labile Enterotoxin as Safe and Strong Adjuvants of Intranasal Delivery of Vaccines", Expert Rev. Vaccines, 2:285-93 (2003).
Pizza, et al., "LTK63 and LTR72, Two Mucosal Adjuvants Ready for Clinical Trials", Int. J. Med. Microbiol., 290:455-61 (2000).
Plante, et al., "Intranasal Immunization with gonococcal outer membrane preparations reduces the duration of vaginal colonization of mice by Neisseria gonorrhoeae", J Infectious Disease 182:848-855 (2000).
Porro, "Specific Antibodies to Diphtheria Toxin and Type 6A Pneumococcal Capsular Polysaccharide Induced by a Model of Semi-Synthetic Glycoconjugate Antigen", Mol. Immunol., 22, 907-919 (1985).
Prausnitz, et al., "Microneedle-Based Vaccines", Curr. Top. Microbiol. Immunol., 333:369-93 (2009).
Quan, et al., "Stabilization of Influenza Vaccine Enhances Protection by Microneedle Delivery in the Mouse Skin" PLoS ONE, 4(9):e7152 (2009).
Rosenberg, et al., "TLR Reporter Cell Lines for Screening TLR Agonists and Antagonists," J. Immunol., Meeting Abstract, 184:136.20 (2010).
Ruan, et al., "Protein D of *Haemophilius influenaza* a Novel Bacterial Surface Protein With Affinity for Human Igd" J. Immunol., 145:3379-3384 (1990).
Sullivan, et al., "Dissolving Polymer Microneedle Patches for Influenza Vaccination", Nature Med., 16:915-920 (2010).
Talkington et al., "Protection of Mice Against Fatal Pneumococcal Challenge by Immunization With Pneumococcal Surface Adhesion A (PsaA)", Microb. Pathog. 21(1):17-22 (1996).
Treanor, et al., "Evaluation of a Recombinant Hemagglutinin Expressed in Insect Cells as an Influenza Vaccine in Young and Elderly Adults", J. Infect. Dis., 173:1467-70 (1996).
Tritto, et al., "The Acquired Immune Response to the Mucosal Adjuvant LTK63 Imprints the Mouse Lung With a Protective Signature", J. Immunol., 179:5346-5357 (2007).
Vrdoljak, et al., "Coated microneedle arrays for transcutaneous delivery of live virus vaccines" J. Control. Release, 159:34-42 (2012).
Whalan et al., "Piva and Piaa, Iron Uptake Lipoproteins of *Streptococcus pneumoniae*, Elicit Serotype Independent Antibody

(56) References Cited

OTHER PUBLICATIONS

Responses Following Human Pneumococcal Septicaemia", FEMS Immunol. Med. Microbiol. 43:73-80 (2005).

* cited by examiner

INTRADERMAL DELIVERY OF IMMUNOLOGICAL COMPOSITIONS COMPRISING TOLL-LIKE RECEPTOR 7 AGONISTS

This application is the US National Stage of International Application No. PCT/EP2014/051860, filed 30 Jan. 2014, which claims benefit of the filing date of U.S. Provisional Application No. 61/759,751, filed 1 Feb. 2013, and EP 13169596.7, filed 28 May 2013, all of which are incorporated herein by reference.

TECHNICAL FIELD

This invention is in the field of vaccine delivery.

BACKGROUND ART

Vaccine compositions comprising Toll-like receptor (TLR) agonists are currently available and these vaccines are administered by intramuscular injection. Although effective, intramuscular administration can cause pain and local tissue damage, and fear of intramuscular injection is common. Intramuscular injections must be administered by medically trained personnel, preventing quick administration and over-the counter sale. Intramuscular administration requires the use of liquid formulations which may lack stability over long periods of time.

It is an object of the invention to provide a different method of administering vaccines comprising TLR agonists, and in particular a more convenient way which do not suffer from the drawbacks mentioned above.

DISCLOSURE OF THE INVENTION

The inventors have surprisingly found that immunogenic compositions comprising a Toll-like receptor (TLR) agonist can provide a better immune response if they are delivered intradermally rather than intramuscularly. Increased numbers of cells expressing TLRs can be found in the dermis and epidermis in comparison to in the muscles, which may explain the improved response provided. Moreover, intradermal delivery can cause significantly less pain than intramuscular delivery and can more easily permit self-administration of the composition, particularly when the intradermal delivery is achieved through use of multiple microneedles in the form of a microneedle device such as a skin patch. Accordingly, the invention provides a method of intradermally delivering an immunogenic composition comprising a TLR agonist and an immunogen.

The invention also provides an intradermal delivery system comprising an immunogenic composition comprising a TLR agonist and an immunogen.

The invention also provides an intradermal delivery system comprising a solid immunogenic composition comprising a TLR agonist, an immunogen and a microneedle.

The invention also provides an intradermal delivery system comprising a solid biodegradable microneedle, wherein the microneedle comprises a TLR agonist and an immunogen.

The invention also provides an intradermal delivery system comprising a solid microneedle, wherein the microneedle comprises a TLR agonist and a bacterial antigen.

The invention also provides an intradermal delivery system comprising a coated microneedle, wherein the microneedle comprises a TLR agonist and an immunogen, wherein the TLR agonist is selected from a TLR2, TLR4, TLR5, TLR1, TLR6, TLR8 and a TLR9 agonist.

The invention also provides an intradermal delivery system comprising an immunogenic composition comprising a TLR agonist, wherein the TLR agonist is:
(a) a benzonaphthyridine TLR7 agonist;
(b) a TLR7 agonist having formula T1:

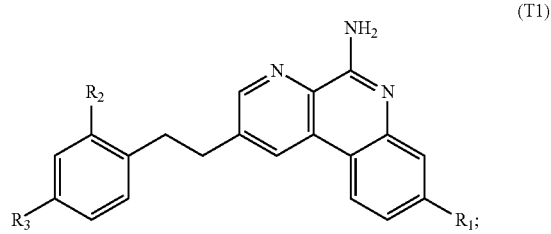

(c) a TLR2 agonist having formula T2:

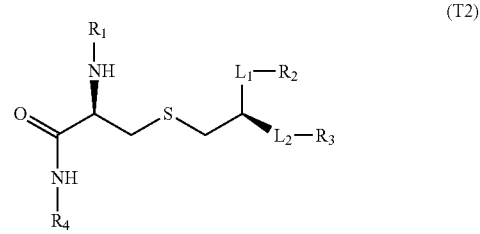

The invention also provides an intradermal delivery system comprising a solid immunogenic composition comprising a TLR agonist, an immunogen and a microneedle, wherein the TLR agonist is selected from a TLR2, TLR3, TLR4, TLR5, TLR1, TLR6, TLR8 and a TLR9 agonist, and the immunogen is not an influenza antigen.

The invention also provides an intradermal delivery system comprising an immunogenic composition comprising a TLR3 agonist and an immunogen, wherein the immunogen is not an influenza antigen.

The invention also provides an intradermal delivery system comprising an immunogenic composition comprising a TLR2 agonist and an immunogen, wherein the immunogen is a viral antigen, a bacterial antigen, a fungal antigen or a tumor antigen.

The invention also provides an intradermal delivery system comprising an immunogenic composition comprising a TLR agonist and an immunogen, wherein the TLR agonist is selected from a TLR5 agonist, a TLR1 agonist and a TLR6 agonist.

The immunogenic composition may comprise a hollow needle. The hollow needle may be a hollow microneedle.

The invention also provides a process for preparing an intradermal delivery system or a skin patch of the invention. The process may comprise i) concentrating an antigen; ii) adding a TLR agonist to the concentrated antigen; iii) formulating an immunogenic composition from the concentrated antigen and the TLR agonist.

The invention also provides a process for preparing an intradermal delivery system comprising a solid microneedle, wherein the microneedle comprises a TLR agonist and an immunogen, wherein the method comprises the steps of a) mixing an immunogen and a TLR agonist to form an immunogenic composition in which the immunogen has a concentration of 10 mg/ml-50 mg/ml and the TLR agonist has a concentration of 0.1 mg/ml-10 mg/ml and b) drying the immunogenic composition to form a solid microneedle.

The concentration of the immunogen may be 10 mg/ml, 15 mg/ml, 20 mg/ml, 25 mg/ml, 30 mg/ml, 35 mg/ml, 40 mg/ml, 45 mg/ml or 50 mg/ml and the concentration of the TLR agonist may be 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 2 mg/ml, 3 mg/ml, 4 mg/ml, 5 mg/ml, 6 mg/ml, 7 mg/ml, 8 mg/ml, 9 mg/ml or 10 mg/ml.

The ratio of antigen to TLR agonist that is used may be around 10:1.

A preferred way of achieving intradermal delivery is via a skin patch (e.g. via a biodegradable microneedle or a coated microneedle) and so the invention also provides a skin patch for intradermal delivery of an immunogen having a plurality of microneedles, wherein the microneedles comprise a TLR agonist and the immunogen.

The immunogenic composition that is delivered intradermally is preferably solid, in contrast to the liquid compositions that are delivered through standard hollow intradermal needles. Solid immunogenic compositions may be in the form of a solid microneedle which can penetrate skin and deliver immunogenic compositions intradermally. The microneedle can itself be formed from the solid immunogenic composition (see solid biodegradable microneedles below), or the microneedle may penetrate the skin to deliver a separate immunogenic composition (see solid coated microneedles below).

The invention also provides an intradermal delivery system comprising an immunogenic composition comprising a CD1d agonist and an immunogen.

The invention also provides an intradermal delivery system comprising an immunogenic composition comprising a CLR agonist and an immunogen.

The invention also provides an intradermal delivery system comprising an immunogenic composition comprising a mutant *E. coli* heat-labile toxin, an immunogen and a microneedle.

Intradermal Delivery

Intradermal delivery of a composition may be achieved using any mode of delivery in which the composition is supplied to the dermis, but does not pass through the dermis to the muscle, including those where the composition is delivered directly to the dermis (e.g. by a needle which passes entirely through the epidermis to the dermis) and those where the composition is first delivered into the epidermis by penetration of the epidermis (e.g. by a needle, where the composition then moves through the epidermis to the dermis). Intradermal delivery contrasts with the intramuscular delivery of the prior art which requires that the delivery system penetrates through both the epidermis (typically about 100 μm thick in humans) and the dermis (typically about 0.6-3 mm thick in humans) and the composition is then delivered into the muscle.

Suitable intradermal delivery systems include, but are not limited to, those based on microneedles. Microneedles are solid, as opposed to hollow, which retain their structural integrity during storage and insertion, and are shaped so that they can penetrate a subject's skin when applied thereto. The mechanical characteristics which are required for skin penetration depend on the target organism, but they preferably have sufficient strength to penetrate human skin whilst remaining substantially intact. Materials for forming suitable needles are readily available (see below) and these can be tested to determine appropriate characteristics for any particular need. Microneedle delivery of vaccines was reviewed in references 1 and 2.

Solid microneedles differ from standard hollow needles because they do not comprise a cavity through which the immunogenic composition passes as a liquid, but rather the form of the microneedle is such that a solid immunogenic composition either is present on the outside of the needle, or itself forms the needle.

The microneedles can penetrate the skin. They are long enough to penetrate through the epidermis to deliver material into the dermis and thus achieve intradermal delivery, but they ideally are not so long that they can penetrate into or past the hypodermis. The length of the needle depends on the target organism, and the length required to reach the dermis of the particular target organism. Therefore for use in humans, they will typically be 100-2500 μm long e.g. about 500 μm, about 1000 μm, or about 1500 μm. At the time of delivery the tip of a microneedle may penetrate the dermis, while its base remains in the epidermis.

The microneedles can have various shapes and geometries e.g. see FIG. 2 of reference 3. They will typically be tapered with a skin-facing point e.g. shaped as pyramids or cones. A tapered microneedle with a widest diameter of <500 μm is typical. Structural parameters (including shape, tip radius, base radius, pitch, height, density, and total pore volume) have been studied in detail (e.g. see references 3-6) and can be modified according to particular needs or desires in any chosen situation.

Microneedles are preferably not used singly but, rather, multiple needles are applied simultaneously using a microneedle device e.g. as a skin patch comprising a plurality of microneedles. A single patch will typically include a plurality of microneedles e.g. $\geq 10$, $\geq 20$, $\geq 30$, $\geq 40$, $\geq 50$, $\geq 60$, $\geq 70$, $\geq 80$, $\geq 90$, $\geq 100$, $\geq 200$, $\geq 300$, $\geq 400$, $\geq 50$, $\geq 750$, $\geq 1000$ or more per patch. Where a patch includes a plurality of microneedles, it may comprise a backing layer to which all of the microneedles are attached. A unitary backing layer with $\geq 20$ projecting microneedles is typical e.g. 50-600 microneedles per patch. Where a patch includes a plurality of microneedles, these can be arranged in a regular repeating pattern or array, or they may be arranged irregularly. Spacing of microneedles can be an important parameter for controlling permeability [3,4] and it can be adjusted according to particular situations.

A patch will typically have an area of 3 cm$^2$ or less, for example <2 cm$^2$ or <1 cm$^2$. A circular patch with a diameter of between 0.5 cm and 1.5 cm is useful.

The density of microneedles on a patch can vary, but may be $\geq 10$ cm$^{-2}$, $\geq 20$ cm$^{-2}$, $\geq 30$ cm$^{-2}$, $\geq 40$ cm$^{-2}$, $\geq 50$ cm$^{-2}$, $\geq 60$ cm$^{-2}$, $\geq 70$ cm$^{-2}$, $\geq 80$ cm$^{-2}$ or more.

A patch of the invention has a skin-facing inner face and an environment-facing outer face. The inner face may include an adhesive to facilitate adherence to a subject's skin. When present, it is preferably not present on the microneedles themselves i.e. the microneedles are adhesive-free. Thus the inner face will typically have an outer adhesive margin or annulus for adhering the patch to skin e.g. as seen in sticking plasters or nicotine patches. The adhesive region and the microneedles can be provided as an integral unit, or the adhesive region can be made by adding a backing which extends outwards beyond the microneedles to provide the outer adhesive margin or annulus for adhering the patch to skin e.g. as seen in sticking plasters or nicotine patches.

Patches may be packaged into individual pouches e.g. sealed under nitrogen, then heat sealed. They should be stored carefully to avoid damage to the microneedles.

Patches of the invention may comprise adhesives which comprise tackifiers. Tackifiers are substances which increase the adhesivity of the patch therefore preventing the patch from falling off the subject's skin. If the immunogenic composition on the inner face of the patch crystallises, the patch can fall off the subject's skin. Therefore crystallisation inhibitors can be added to the immunogenic composition to prevent the composition from crystallising.

Microneedles can be hollow, such that an immunogenic composition can pass through them and thus arrive in the dermis. A preferred option, however, uses solid non-hollow microneedles. Useful solid needles include biodegradable and non-biodegradable needles. Biodegradable needles can (if desired) be left in the skin after being applied, and immunogen can be incorporated into the needles themselves during manufacture, such that immunogen is released as the needles degrade or dissolve in situ. Non-biodegradable solid needles must be removed some time after being applied and immunogen is typically present as a dry coating on the external face of the solid needles.

Solid Biodegradable Microneedles

One useful solid microneedle format for use in the invention is a solid biodegradable microneedle. Immunogen is incorporated within the microneedle, such that the needle is structurally composed of both the immunogen and suitable solid excipients. The solid excipients provide mechanical strength to permit the microneedles to be inserted into a subject's skin, where the immunogen can be released.

The microneedles are biosoluble and biodegradable. Thus the needle can dissolve in the skin after the microneedle is applied, in contrast to the coated microneedles used in references 7 & 8 (see below). Having dissolved, the needle material will then be metabolised to give harmless end-products. The timescale for dissolving after applying the patch can vary, but dissolving will typically commence immediately after applying the patch (e.g. within 10 seconds) and may continue for e.g. up to 1 minute, 5 minutes, 10 minutes, 20 minutes, 30 minutes, 1 hour, 5 hours, 10 hours, or 24 hours, until the microneedle has fully dissolved (although the needles might be removed before dissolution is complete). Materials with suitable in vivo dissolving kinetics are readily available (as described below) and these can be varied and tested to determine appropriate concentrations etc. for any desired dissolution profile.

Suitable materials for forming the microneedles will typically be biosoluble and biodegradable polymers, and these may comprise one or more carbohydrates. Short-chain carbohydrates can also be used. For example, the material may comprise a cellulose, a dextrin, a dextran, a disaccharide, a chitosan, a chitin, etc., or mixtures thereof. Hyaluronates can also be used [9], as can polylactic acids [10]. As an alternative to carbohydrate materials, polymers such as polyvinylpyrrolidone (PVP) can be used, or copolymers of methylvinylether and either maleic acid or maleic anhydride (PMVE/MA), such as Gantrez™ AN-139 [6,11]. Other GRAS materials may also be used.

Suitable celluloses include, but are not limited to, cellulose, carboxymethyl-celluloses, hydroxypropyl-celluloses, hydroxyethyl cellulose, and hydroxypropyl methylcellulose. Suitable dextrins include, but are not limited to, maltodextrin, cyclodextrin, amylodextrin, icodextrin, yellow dextrin, and white dextrins. Suitable disaccharides include, but are not limited to, sucrose, lactose, maltose, trehalose, turanose, and cellobiose. One suitable material for forming biosoluble and biodegradable microneedles is a dextrin/trehalose mixture. Further suitable carbohydrates are amylopectins [12]. Formulation excipients can easily be added to the immunogenic compositions of the solid biodegradable microneedles to improve stability of the composition and to provide a process of manufacture which is both robust and scalable. The polymers of solid biodegradable microneedles can provide the advantage of stabilising antigens. Such an advantage may be provided by the polymers of the microneedles or co-polymers having carbohydrate groups which have a stabilising effect on the antigens. Shelf life of the intradermal delivery system can therefore be extended.

The antigen capacity of solid biodegradable microneedles can be higher than other microneedles, which provides the advantage of allowing usability in combination with antigens which require high levels of immunogen to be provided in each needle, such as tetravalent influenza, These needles can be made in various ways e.g. by following the techniques and guidance in references 12 to 19. For instance, a mold with microneedle cavities can be prepared. A matrix material (e.g. a mixture of dextrin and trehalose) can be combined with an immunogen and this aqueous material is then centrifugally cast in the mold to form an array of solid microneedles. A cellulose gel can then be cast over the matrix/immunogen mixture (e.g. which mixture has formed a film) to form a backing layer on the patch. When this backing layer has dried, it can be removed to give a patch from which the solid microneedles project. An alternative method involves the in situ polymerisation in a suitable mold e.g. an immunogen can be mixed with a liquid monomer (such as vinyl pyrrolidone) within a patch mold and this mixture can be photopolymerised. In such a process the immunogen is ideally present in dried (e.g. lyophilised) form such that it becomes encapsulated during polymerisation. Molding of hydrogels [12] or particles [20] can also be used. Molds for these processes can be made in various ways e.g. by laser-based micromolding [6], by etching, etc.

Thus a manufacturing process may comprise: (a) mixing a biosoluble and biodegradable matrix material with an immunogen, usually by reconstituting a lyophilised immunogen; (b) adding the mixture from step (a) to a mold containing cavities for forming microneedles; (c) letting the mixture set in the mold, to form solid microneedles; (d) optionally, applying material to the set microneedles to provide a backing layer; and (e) removing the microneedles (and optional backing layer) from the mold. An alternative manufacturing process may comprise: (a) mixing a polymerisable monomer with an immunogen, usually a lyophilised immunogen; (b) adding the mixture from step (a) to a mold containing cavities for forming microneedles; (c) polymerising monomer within the mixture in the mold, to form solid microneedles; (d) optionally, applying material to the solid microneedles to provide a backing layer; and (e) removing the microneedles (and optional backing layer) from the mold.

Solid biodegradable microneedles are ideally provided as an array on a patch. As mentioned above, the patch can have two portions, which can suitably take the form of an inner disc and an outer annulus. The microneedles may be provided on a first inner portion of the patch, and a second outer portion can include an adhesive. This patch can be placed on the skin and pressed down so that the outer portion adheres to the skin, while the microneedles on the inner portion penetrate the epidermis. Such arrays may be produced by soft lithography or photolithography.

Dissolving microneedle arrays were shown in reference 21 to be suitable for eliciting protection against tetanus, diphtheria, malaria, and influenza (see also reference 16). Solid biodegradable microneedles are advantageous over other forms of needles due to the lack of sharp surfaces on the needle. Therefore solid biodegradable needles provide increased levels of safety and may allow for over the counter sale and self-administration.

Furthermore, formulation of immunogenic compositions as solid biodegradable microneedles can be achieved more easily that the immunogenic compositions used with the solid coated microneedles discussed below. Many immunogenic compositions comprise detergents, particularly those based on viral surface antigens. These detergents can cause difficulties when preparing coated microneedles, so biodegradable microneedles provide an advantage for such compositions.

Solid Coated Microneedles

Another useful solid microneedle format for use in the invention is a solid, non-hollow, non-biodegradable microneedle. The microneedle is made from a material which has mechanical strength to permit insertion into a subject's skin. Immunogen is coated onto the needles and, after they have been injected, immunogen is released from the coating. The MACROFLUX™ (Zosano), MTS™ (3M) and IMMUNPATCH™ technologies are examples of such delivery systems.

The microneedles are solid and remain intact after insertion into a patient's skin (in contrast to the biodegradable microneedles discussed above). Materials for forming suitable solid needles are readily available and these can be tested and selected for any particular need e.g. metals (such as stainless steel), polymers (such as polycarbonate, ideally medical grade), or silicon. Metal needles can be fabricated by using laser cutting and electro-polishing [24] or etching [22]. Polymer needles can be fabricated by microreplication and/or micromolding (including injection molding). Silicon needles can be made by etching [4,23]. Suitable microneedles are disclosed in references 7, 8, and 24-28.

Immunogen is coated onto the microneedles. Coating may be achieved by applying either a liquid coating which then forms a solid coating (e.g. by drying), or by applying a solid coating directly. Coating can be achieved by a simple process such as dip-coating e.g. involving a dipping step then a drying step (e.g. by evaporation), with repetition as required. Other useful coating techniques are disclosed in reference 26. Spray coating can also be used, with sugar-based formulations to provide a dry coating [29]. Thus a process of the invention may comprise: applying an immunogen to the surface of one or more solid microneedles to provide a coated microneedle device for injection of the vaccine.

A coating solution for applying to the needles can include one or more biosoluble and biodegradable matrix materials, such as those discussed above for formation of biodegradable needles, and in particular by incorporating carbohydrates. Thus a process of the invention may comprise: (a) mixing a biosoluble and biodegradable matrix material with an immunogen; and (b) applying the mixture from step (a) to the surface of one or more solid microneedles to provide a coated microneedle device for injection of the immunogen. Coating may be enhanced by using one or more "deposition enhancing components" as described in reference 26.

The applying steps discussed above may comprise an application sub-step followed by a drying sub-step, and this pair of sub-steps can be performed once or more than once e.g. 1, 2, 3, 4, 5, 6, 7, 8, 9, 10 or more times.

Coated solid microneedle arrays were used in reference 22 with influenza virus immunogens and were shown to activate both humoral and cellular arms of the immune response and confer improved long-term protection.

Toll-Like Receptor Agonists

Compositions of the invention include a TLR agonist i.e. a compound which can agonise a Toll-like receptor. Most preferably, a TLR agonist is an agonist of a human TLR. The TLR agonist can activate any of TLR1, TLR2, TLR3, TLR4, TLR5, TLR6, TLR7, TLR8, TLR9 or TLR11; preferably it can activate human TLR4 or human TLR7.

A composition of the invention can include more than one TLR agonist. These two agonists are different from each other and they can target the same TLR or different TLRs.

Agonist activity of a compound against any particular Toll-like receptor can be determined by standard assays. Companies such as Imgenex and Invivogen supply cell lines which are stably co-transfected with human TLR genes and NFκB, plus suitable reporter genes, for measuring TLR activation pathways. They are designed for sensitivity, broad working range dynamics and can be used for high-throughput screening. Constitutive expression of one or two specific TLRs is typical in such cell lines. See also reference 30. Many TLR agonists are known in the art e.g. reference 31 describes certain lipopeptide molecules that are TLR2 agonists, references 32 to 35 each describe classes of small molecule agonists of TLR7, and references 36 & 37 describe TLR7 and TLR8 agonists for treatment of diseases.

TLR7 agonists which can be used with the invention can be benzonaphthyridines, such as those having formula T1:

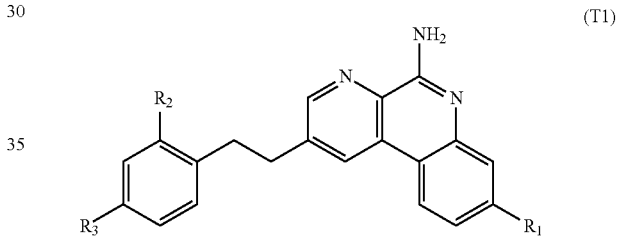

(T1)

where
$R^1$ is H, $C_1$-$C_6$alkyl, —$C(R^5)_2OH$, -$L^1R^5$, -$L^1R^6$, -$L^2R^5$, -$L^2R^6$, —$OL^2R^5$, or —$OL^2R^6$;
$L^1$ is —C(O)— or —O—;
$L^2$ is $C_1$-$C_6$alkylene, $C_2$-$C_6$alkenylene, arylene, heteroarylene or $((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;
each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;
$L^4$ is arylene or heteroarylene;
$R^2$ is H or $C_1$-$C_6$alkyl;
$R^3$ is selected from $C_1$-$C_4$alkyl, -$L^3R^5$, -$L^1R^5$, -$L^3R^7$, -$L^3L^4R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2OH$;
each $R^4$ is independently selected from H and fluoro;
$R^5$ is —$P(O)(OR^9)_2$,
$R^6$ is —$CF_2P(O)(OR^9)_2$ or —$C(O)OR^{10}$;
$R^7$ is —$CF_2P(O)(OR^9)_2$ or —$C(O)OR^{10}$;
$R^8$ is H or $C_1$-$C_4$alkyl;
each $R^9$ is independently selected from H and $C_1$-$C_6$alkyl;
$R^{10}$ is H or $C_1$-$C_4$alkyl;
each p is independently selected from 1, 2, 3, 4, 5 and 6, and
q is 1, 2, 3 or 4.

Further details of these compounds are disclosed in reference 38, and the invention can use any of compounds 1 to 28 from reference 38. Preferred examples of compounds of formula T1 include:

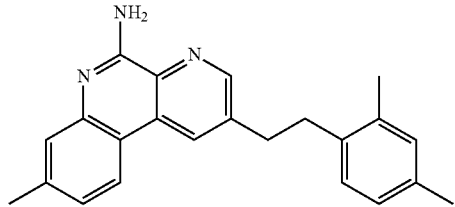

T1a

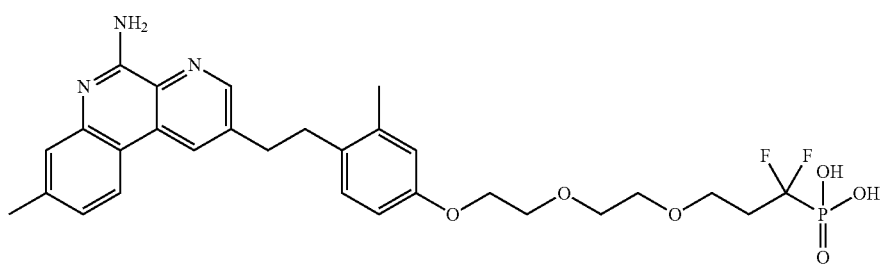

T1b

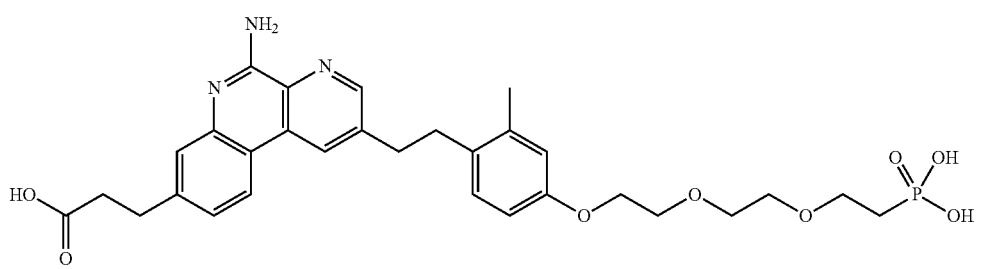

T1c

Other useful TLR7 agonists include, but are not limited to, or any of compounds 1 to 247 disclosed in reference 34, or any of compounds 1 to 102 from reference 39.

TLR2 agonists which can be used with the invention can be lipopeptides having formula T2:

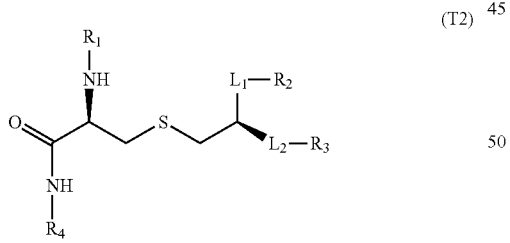

(T2)

wherein:
$R^1$ is H, —C(O)—$C_7$-$C_{18}$alkyl or —C(O)— $C_1$-$C_6$alkyl;
$R^2$ is $C_7$-$C_{18}$alkyl;
$R^3$ is $C_7$-$C_{18}$alkyl;
$L_1$ is —$CH_2$OC(O)—, —$CH_2$O—, —$CH_2$NR$^7$C(O)— or —$CH_2$OC(O)NR$^7$—;
$L_2$ is —OC(O)—, —O—, —NR$^7$C(O)— or —OC(O)NR$^7$—;
$R^4$ is -$L_3R^5$ or -$L_4R^5$;
$R^5$ is —N($R^7$)$_2$, —OR$^7$, —P(O)(OR$^7$)$_2$, —C(O)OR$^7$, —NR$^7$C(O)$L_3R^8$, —NR$^7$C(O)$L_4R^8$, —O$L_3R^6$, —C(O)NR$^7L_3R^8$, —C(O)NR$^7L_4R^8$, —S(O)$_2$OR$^7$, —OS(O)$_2$OR$^7$, $C_1$-$C_6$alkyl, a $C_6$aryl, a $C_{10}$aryl, a $C_{14}$aryl, 5 to 14 ring membered heteroaryl containing 1 to 3 heteroatoms selected from O, S and N, $C_3$-$C_8$cycloalkyl or a 5 to 6 ring membered heterocycloalkyl containing 1 to 3 heteroatoms selected from O, S and N, wherein the aryl, heteroaryl, cycloalkyl and heterocycloalkyl of $R^5$ are each unsubstituted or the aryl, heteroaryl, cycloalkyl and heterocycloalkyl of $R^5$ are each substituted with 1 to 3 substituents independently selected from —OR$^9$, —O$L_3R^6$, —O$L_4R^6$, —OR$^7$, and —C(O)OR$^7$;

$L_3$ is a $C_1$-$C_{10}$alkylene, wherein the $C_1$-$C_{10}$alkylene of $L_3$ is unsubstituted, or the $C_1$-$C_{10}$alkylene of $L_3$ is substituted with 1 to 4 $R^6$ groups, or the $C_1$-$C_{10}$alkylene of $L_3$ is substituted with 2 $C_1$-$C_6$alkyl groups on the same carbon atom which together, along with the carbon atom they are attached to, form a $C_3$-$C_8$cycloakyl;

$L_4$ is —(($CR^7R^7)_pO)_q(CR^{10}R^{10})_p$— or —($CR^{11}R^{11}$)(($CR^7R^7)_pO)_q(CR^{10}R^{10})_p$—, wherein each $R^{11}$ is a $C_1$-$C_6$alkyl groups which together, along with the carbon atom they are attached to, form a $C_3$-$C_8$cycloakyl;

each $R^6$ is independently selected from halo, $C_1$-$C_6$alkyl, $C_1$-$C_6$alkyl substituted with 1-2 hydroxyl groups, —OR$^7$, —N($R^7$)$_2$, —C(O)OH, —C(O)N($R^7$)$_2$, —P(O)(OR$^7$)$_2$, a $C_6$aryl, a $C_{10}$aryl and a $C_{14}$aryl;

each $R^7$ is independently selected from H and $C_1$-$C_6$alkyl;

$R^8$ is selected from —SR$^7$, —C(O)OH, —P(O)(OR$^7$)$_2$, and a 5 to 6 ring membered heterocycloalkyl containing 1 to 3 heteroatoms selected from O and N;

$R^9$ is phenyl;

each $R^{10}$ is independently selected from H and halo;

each p is independently selected from 1, 2, 3, 4, 5 and 6, and q is 1, 2, 3 or 4.

Further details of these compounds are disclosed in reference 40, and the invention can use any of the compounds disclosed therein e.g. examples 1-92 thereof, and the compounds listed in claim 17 thereof. Another useful TLR2 agonist is palmitoyl-Cys(2[R],3-dilauroyloxy-propyl)-Abu-D-Glu-NH$_2$, where: Cys is a cysteine residue, Abu is an aminobutyric acid residue and Glu is a glutamic acid residue. This compound is disclosed in example 16 of re. 31, and has formula T3a:

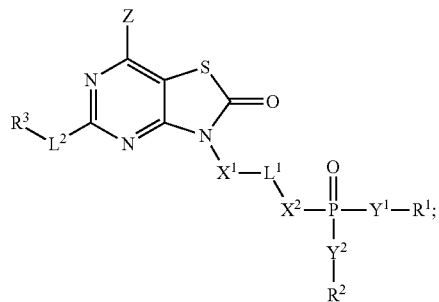

as defined on pages 2-5 & 7-8 of ref. 33

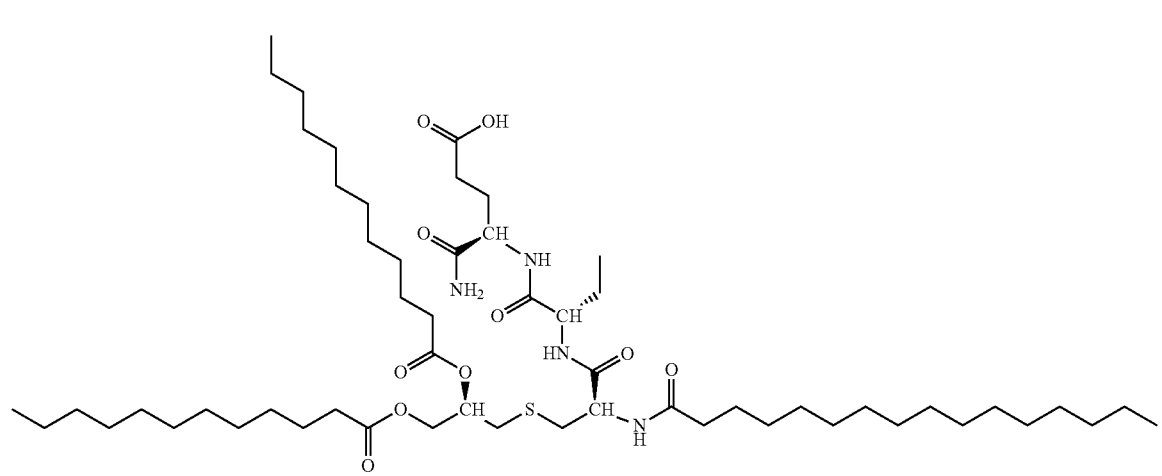

(T3a)

The agonist of formula T1 or T2 or T3a can be present as a pharmaceutically acceptable salt, a pharmaceutically acceptable solvate (e.g. hydrate), as a N-oxide derivative, as an isomer (including a tautomer or an enantiomer) or a mixture of isomers, etc. One particularly useful salt is the arginine salt of compound T1c, which can be used as the arginine salt monohydrate.

Other useful TLR agonists are the following compounds:

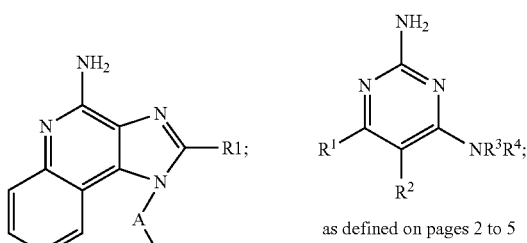

as defined on pages 6 and 7 of reference 32 as defined on pages 2 to 5 of reference 35

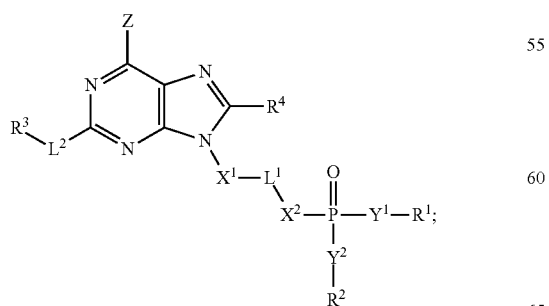

as defined on pages 2-7 of reference 33

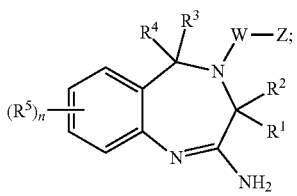

as defined on pages 5 to 6 of reference 36

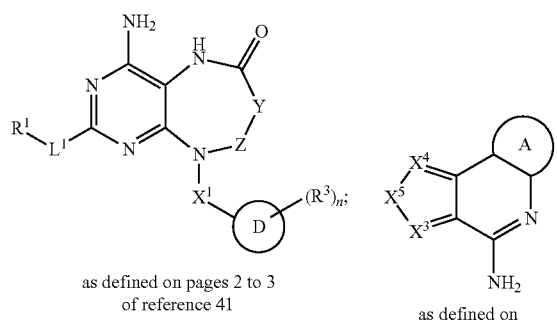

as defined on pages 2 to 3
of reference 41 as defined on
pages 2-4
of reference 34

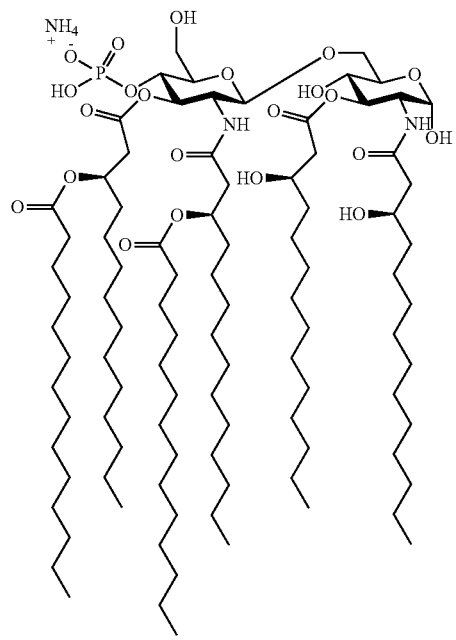

Various useful TLR4 agonists are known in the art, many of which are analogs of endotoxin or lipopolysaccharide (LPS), or of monophosphoryl lipid A ('MPLA'). For instance, a TLR4 agonist used with the invention can be:

(i) 3d-MPL (i.e. 3-O-deacylated monophosphoryl lipid A; also known as 3-de-O-acylated monophosphoryl lipid A or 3-O-desacyl-4'-monophosphoryl lipid A). This derivative of the monophosphoryl lipid A portion of endotoxin has a de-acylated position 3 of the reducing end of glucosamine. It has been prepared from a heptoseless mutant of *Salmonella minnesota*, and is chemically similar to lipid A but lacks an acid-labile phosphoryl group and a base-labile acyl group. Preparation of 3d-MPL was originally described in ref. 42, and the product has been manufactured and sold by Corixa Corporation. It is present in GSK's 'AS04' adjuvant. Further details can be found in references 43 to 46.

(ii) glucopyranosyl lipid A (GLA) [47] or its ammonium salt e.g.

(iii) an aminoalkyl glucosaminide phosphate, such as RC-529 or CRX-524 [48-50]. RC-529 and CRX-524 have the following structure, differing by their $R_2$ groups:

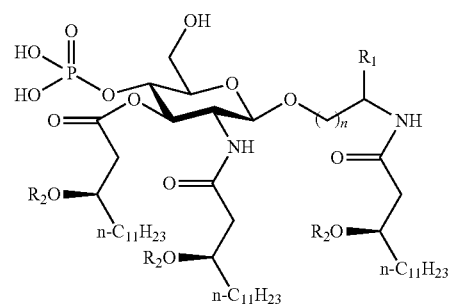

$R_1$ = H, $R_2$ = n-$C_{13}H_{27}$CO, n = 1 (RC-529)
$R_1$ = H, $R_2$ = n-$C_9H_{19}$CO, n = 1 (CRX-524)

(iv) compounds containing lipids linked to a phosphate-containing acyclic backbone, such as E5564 [51,52]:

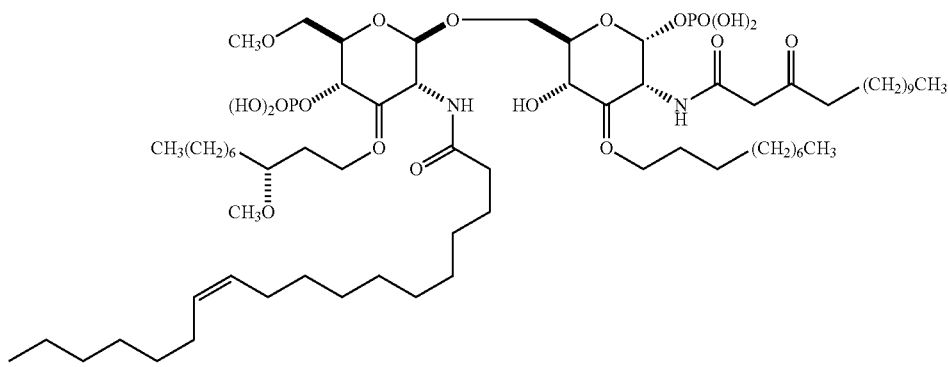

(v) A compound of formula I, II or III as defined in reference 53, or a salt thereof, such as compounds 'ER 803058', 'ER 803732', 'ER 804053', 'ER 804058', 'ER 804059', 'ER 804442', 'ER 804680', 'ER 803022', 'ER 804764' or 'ER 804057'. ER 804057 is also known as E6020 and it has the following structure:

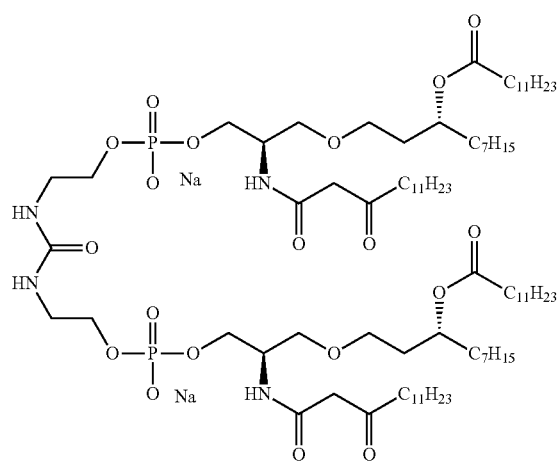

whereas ER 803022 has the following structure:

(vi) One of the polypeptide ligands disclosed in reference 54.

Preferred TLR4 agonists are analogs of monophosphoryl lipid A (MPL)

Other Biological Receptors

The invention is defined above and below by reference to TLR agonists, but it can be more widely applied to other small molecule immunopotentiators (SMIPs) which do not act via TLRs. In particular, SMIPs which may be used with the invention may agonise C-type lectin receptors (CLRs) or CD1d rather than (or in addition to) a TLR. Thus the present disclosure includes the invention as described above with reference to TLR agonism, but wherein references to a TLR agonist (or similar) are replaced by reference either to a CLR agonist or to a CD1d agonist.

CLR agonists include, but are not limited to, trehalose-6,6'-dimycolate (TDM), its synthetic analog D-(+)-trehalose-6,6'-dibehenate (TDB), and other 6,6'-diesters of trehalose and fatty acids. Thus the invention can be applied to trehalose esters and diacyl trehaloses which are CLR agonists. These agonists may have formula (C):

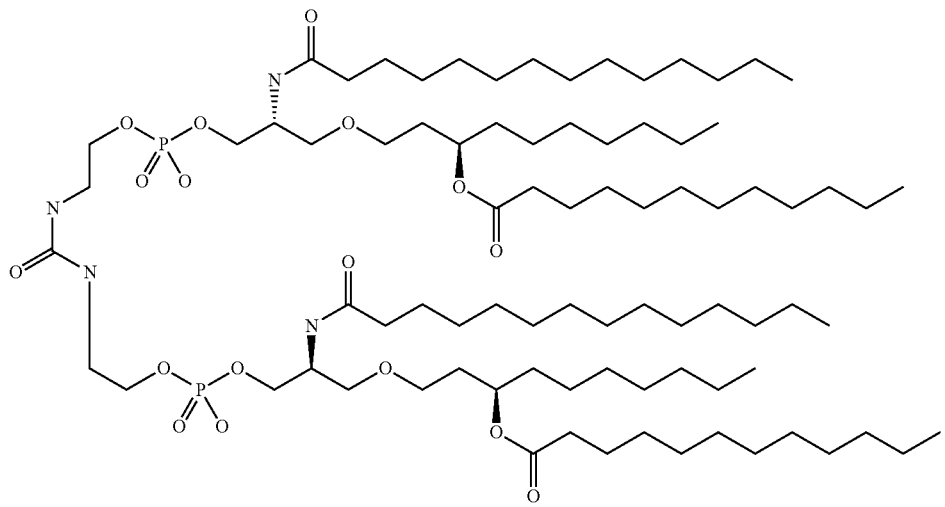 [SMILES: CCCCCCCCCCCCCC(=O)N[C@H](COCC[C@@H](CCCCCCC)OC(=O)CCCCCCCCCCC)COP(=O)(O)OCCNC(=O)NCCOP(=O)(O)OC[C@H](COCC[C@@H](CCCCCCC)OC(=O)CCCCCCCCCCC)NC(=O)CCCCCCCCCCCCC]

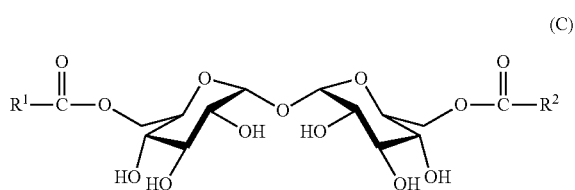

(C)

where R¹C(O)— and R²C(O)— are the same or different and are acyl groups. Suitable acyl groups may be saturated or unsaturated. They may be selected from the acyl residues of a mycolic acid, a corynomycolic acid, a 2-tetradecyl-3-hydroxyoctadecanoic acid, a 2-eicosyl-3-hydroxytetracosanoic acid, a bourgeanic acid, a behenic acid, a palmitic acid, etc. Useful mycolic acids include alpha-, methoxy-, and keto-mycolic acids, in cis- and or trans-forms.

CD1d agonists include, but are not limited to, α-glycosylceramides [55-64] such as α-galactosylceramides. Thus the invention can be applied to glycosylceramides which are CD1d agonists, including α-galactosylceramide (α-GalCer), phytosphingosine-containing α-glycosylceramides, [(2S,3S,4R)-1-O-(α-D-galactopyranosyl)-2-(N-hexacosanoylamino)-1,3,4-octadecanetriol], OCH, KRN7000 CRONY-101, 3″-O-sulfo-galactosylceramide, etc.

Mutant *E. coli* Heat-Labile Toxin

The invention is defined above and below by reference to TLR agonists, but it can also be applied to proteinaceous adjuvants which do not act via TLRs, such as mutant *E. coli* heat-labile toxins. Thus the present disclosure includes the invention as described above with reference to TLR agonism, but wherein references to a TLR agonist (or similar) are replaced by reference to a mutant *E. coli* heat-labile toxin which displays reduced enzymatic activity compared to the wild-type toxin [65,66,67]. Various such mutants are known e.g. reference 68.

Suitable mutant *E. coli* heat-labile toxins include, but are not limited to, a K63 mutant (in which the wild-type Ser-63 in the enzymatically active A-subunit is mutated to Lys [68,69]) and a R72 mutant (in which wild-type Ala-72 is mutated to Arg [69,70]), or a double K63/R72 mutant [71]. The G192 mutant can also be used, in which wild-type Arg is mutated to Gly.

Immunogens

The invention can be used to deliver a wide range of immunogens, for treating or protecting against a wide range of diseases. The immunogen may elicit an immune response that protects against a viral disease (e.g. due to an enveloped or non-enveloped virus), a bacterial disease (e.g. due to a Gram negative or a Gram positive bacterium), a fungal disease, a parasitic disease, an auto-immune disease, or any other disease. The immunogen may also be useful in immunotherapy e.g. for treating a tumour/cancer, Alzheimer's disease, or an addiction.

The immunogen may take various forms e.g. a whole organism, an outer-membrane vesicle, a polypeptide, a saccharide, a liposaccharide, a conjugate (e.g. of a carrier and a hapten, or of a carrier and a saccharide), etc. Where the immunogen is a polypeptide, it will typically be a surface polypeptide e.g. an adhesin, a hemagglutinin, an envelope glycoprotein, a spike glycoprotein, etc.

The immunogen may be produced by expression in an organism that differs from the organism which causes the disease which the immunogen provides an immune response against. However, a viral immunogen is an immunogen which elicits an immune response against a viral disease, even if the viral immunogen is expressed in a bacterium. Similarly, an immunogen that elicits an immune response against a bacterial disease is a bacterial immunogen, irrespective of how the immunogen was produced. For example, an HIV immunogen that is expressed in *E. coli* is a viral immunogen, rather than a bacterial immunogen.

Viral Antigens

Viral antigens suitable for use in the immunogenic compositions provided herein include, but are not limited to, inactivated (or killed) virus, attenuated virus, split virus formulations, purified subunit formulations, viral proteins which may be isolated, purified or derived from a virus, Virus Like Particles (VLPs) and polynucleotide antigens which may be isolated, purified or derived from a virus or recombinantly synthesized. In certain embodiments, viral antigens are derived from viruses propagated on cell culture or other substrate. In other embodiments, viral antigens are expressed recombinantly. In certain embodiments, viral antigens preferably include epitopes which are exposed on the surface of the virus during at least one stage of its life cycle. Viral antigens are preferably conserved across multiple serotypes or isolates. Viral antigens suitable for use in the immunogenic compositions provided herein include, but are not limited to, antigens derived from one or more of the viruses set forth below as well as the specific antigens examples identified below.

Orthomyxovirus: Viral antigens include, but are not limited to, those derived from an Orthomyxovirus, such as Influenza A, B and C. In certain embodiments, orthomyxovirus antigens are selected from one or more of the viral proteins, including hemagglutinin (HA), neuraminidase (NA), nucleoprotein (NP), matrix protein (M1), membrane protein (M2), one or more of the transcriptase components (PB1, PB2 and PA). In certain embodiments the viral antigen include HA and NA. In certain embodiments, the influenza antigens are derived from interpandemic (annual) flu strains, while in other embodiments, the influenza antigens are derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens include, but are not limited to, those derived from Paramyxoviridae viruses, such as Pneumoviruses (RSV), Paramyxoviruses (PIV), Metapneumovirus and Morbilliviruses (Measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. In other embodiments, pneumovirus antigens include F, G and M. In certain embodiments, pneumovirus antigens are also formulated in or derived from chimeric viruses, such as, by way of example only, chimeric RSV/PIV viruses comprising components of both RSV and PIV.

Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin-Neuraminidase (FIN), Fusion proteins F1 and F2, Nucleoprotein (NP), Phosphoprotein (P), Large protein (L), and Matrix protein (M). In other embodiments, paramyxovirus proteins include HN, F1 and F2. In certain embodiments, paramyxovirus antigens are also formulated in or derived from chimeric viruses, such as, by way of example only, chimeric RSV/PIV viruses comprising components of both RSV and PIV. Commercially available mumps vaccines include live attenuated mumps virus, in either a monovalent form or in combination with measles and rubella vaccines (MMR). In other embodiments, the Paramyxovirus is Nipahvirus or Henipavirus and the anitgens are selected from one or more of the following proteins: Fusion (F) protein, Glycoprotein (G) protein, Matrix (M) protein, Nucleocapsid (N) protein, Large (L) protein and Phosphoprotein (P).

Poxviridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M. In certain embodiments, metapneumovirus antigens are also formulated in or derived from chimeric viruses.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens include, but are not limited to, those derived from Picornaviruses, such as Enteroviruses, Rhinoviruses, Heparnavirus, Cardioviruses and Aphthoviruses. In certain embodiments, the antigens are derived from Enteroviruses, while in other embodiments the enterovirus is Poliovirus. In still other embodiments, the antigens are derived from Rhinoviruses. In certain embodiments, the antigens are formulated into virus-like particles (VLPs).

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the antigens are derived from Enteroviruses, while in other embodiments the enterovirus is Poliovirus. In certain embodiments, the enterovirus antigens are selected from one or more of the following Capsid proteins VP0, VP1, VP2, VP3 and VP4. Commercially available polio vaccines include Inactivated Polio Vaccine (IPV) and Oral poliovirus vaccine (OPV). In certain embodiments, the antigens are formulated into virus-like particles.

Bunyavirus: Viral antigens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Rhinovirus: Viral antigens include, but are not limited to, those derived from rhinovirus. In certain embodiments, the rhinovirus antigens are selected from one or more of the following Capsid proteins: VP0, VP1, VP2, VP2 and VP4. In certain embodiments, the antigens are formulated into virus-like particles (VLPs).

Heparnavirus: Viral antigens include, but are not limited to, those derived from a Heparnavirus, such as, by way of example only, Hepatitis A virus (HAV). Commercially available HAV vaccines include inactivated HAV vaccine.

Togavirus: Viral antigens include, but are not limited to, those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected from E1, E2 or E3. Commercially available Rubella vaccines include a live cold-adapted virus, typically in combination with mumps and measles vaccines (MMR).

Flavivirus: Viral antigens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E. Commercially available TBE vaccine includes inactivated virus vaccines. In certain embodiments, the antigens are formulated into virus-like particles (VLPs).

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe). Commercially available HBV vaccines include subunit vaccines comprising the surface antigen S protein.

Hepatitis C virus: Viral antigens include, but are not limited to, those derived from a Hepatitis C virus (HCV). In certain embodiments, the HCV antigens are selected from one or more of E1, E2, E1/E2, NS345 polyprotein, NS 345-core polyprotein, core, and/or peptides from the nonstructural regions. In certain embodiments, the Hepatitis C virus antigens include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity. In certain embodiments, the antigens are formulated into virus-like particles (VLPs).

Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens include, but are not limited to, those derived from Calciviridae, such as Norwalk virus, and Norwalk-like Viruses, such as Hawaii Virus and Snow Mountain Virus. In certain embodiments, the antigens are formulated into virus-like particles (VLPs).

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (or clades) A, B, C, D, F, G, H, J. K, O. In other embodiments, the antigens are derived from HIV-1 circulating recombinant forms (CRFs), including, but not limited to, A/B, A/E, A/G, A/G/I, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p55 gag and gp140v delete). In certain embodiments, the HIV antigens are derived from one or more of the following strains: HIVIIIb, HIVSF2, HIVLAV, HIVLAI, HIVMN, HIV-1CM235, HIV-1US4, HIV-1SF162, HIV-1TV1, HIV-1MJ4. In certain embodiments, the antigens are derived from endogenous human retroviruses, including, but not limited to, HERV-K ("old" HERV-K and "new" HERV-K).

Reovirus: Viral antigens include, but are not limited to, those derived from a Reovirus, such as an Orthoreovirus, a Rotavirus, an Orbivirus, or a Coltivirus. In certain embodiments, the reovirus antigens are selected from structural proteins λ1, λ2, λ3, μ1, μ2, σ1, σ2, or σ3, or nonstructural proteins σNS, μNS, or σ1s. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Parvovirus, such as Parvovirus B19. In certain embodiments, the Parvovirus antigens are selected from VP-1, VP-2, VP-3, NS-1 and NS-2. In certain embodiments, the Parvovirus antigen is capsid protein VP1 or VP-2. In certain embodiments, the antigens are formulated into virus-like particles (VLPs).

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus: Viral antigens include, but are not limited to, those derived from a Human Herpesvirus, such as, by way of example only, Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins ($\alpha$), early proteins ($\beta$), and late proteins ($\gamma$). In certain embodiments, the HSV antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. A live attenuated VZV vaccine is commercially available. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, US8, US9, US10, US11, US12, US13, US14, US15, US16, US17, US18, US19, US20, US21, US29, US30 and US34A. CMV antigens may also be fusions of one or more CMV proteins, such as, by way of example only, pp65/IE1 (Reap et al., Vaccine (2007) 25:7441-7449). In certain embodiments, the antigens are formulated into virus-like particles (VLPs).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the HPV antigens are formulated into virus-like particles (VLPs). In certain embodiments, the Polyomyavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

Further provided are antigens, compositions, methods, and microbes included in Vaccines, 4$^{th}$ Edition (Plotkin and Orenstein ed. 2004); Medical Microbiology 4$^{th}$ Edition (Murray et al. ed. 2002); Virology, 3rd Edition (W. K. Joklik ed. 1988); Fundamental Virology, 2nd Edition (B. N. Fields and D. M. Knipe, eds. 1991), which are contemplated in conjunction with the immunogenic compositions provided herein.

In a preferred embodiment, the immunogen may elicit an immune response against an influenza virus, including influenza A and B viruses. Various forms of influenza virus immunogen are currently available, typically based either on live virus or on inactivated virus. Inactivated vaccines may be based on whole virions, split virions, or on purified surface antigens. Influenza immunogens can also be presented in the form of virosomes. Hemagglutinin is the main immunogen in current inactivated vaccines, and vaccine doses are standardised by reference to HA levels, typically measured by SRID. Existing vaccines typically contain about 15 µg of HA per strain, although lower doses can be used e.g. for children, or in pandemic situations, or when using an adjuvant. Fractional doses such as ½ (i.e. 7.5 µg HA per strain), ¼ and ⅛ have been used, as have higher doses (e.g. 3× or 9× doses [72,73]). Thus compositions may include between 0.1 and 150 µg of HA per influenza strain, preferably between 0.1 and 50 µg e.g. 0.1-20 µg, 0.1-15 µg, 0.1-10 µg, 0.5-5 µg, etc. Particular doses include e.g. about 45, about 30, about 15, about 10, about 7.5, about 5, about 3.8, about 3.75, about 1.9, about 1.5, etc. per strain. It is usual to include substantially the same mass of HA for each strain included in the vaccine e.g. such that the HA mass for each strain is within 10% of the mean HA mass per strain, and preferably within 5% of the mean. For live vaccines, dosing is measured by median tissue culture infectious dose (TCID$_{50}$) rather than HA content, and a TCID$_{50}$ of between $10^6$ and $10^8$ (preferably between $10^{6.5}$-$10^{7.5}$) per strain is typical. Rather than use SPF eggs as the substrate for viral growth, where virus is harvested from infected allantoic fluids of hens' eggs, cell lines that support influenza virus replication may be used. The cell line will typically be of mammalian origin e.g. MDCK. Influenza A virus immunogens may be from any suitable HA subtype strain e.g. H1, H3, H5, H7, H9 etc., such as a H1N1, H3N2 and/or H5N1 strain.

Bacterial Antigens

Bacterial antigens suitable for use in immunogenic compositions provided herein include, but are not limited to, proteins, polysaccharides, lipopolysaccharides, polynucleotides, and outer membrane vesicles which are isolated, purified or derived from a bacteria. In certain embodiments, the bacterial antigens include bacterial lysates and inactivated bacteria formulations. In certain embodiments, the bacterial antigens are produced by recombinant expression. In certain embodiments, the bacterial antigens include epitopes which are exposed on the surface of the bacteria during at least one stage of its life cycle. Bacterial antigens are preferably conserved across multiple serotypes. In certain embodiments, the bacterial antigens include antigens derived from one or more of the bacteria set forth below as well as the specific antigens examples identified below:

Neisseria meningitidis: N. meningitidis antigens include, but are not limited to, proteins, saccharides (including a polysaccharide, or lipooligosaccharide), or outer-membrane vesicles purified or derived from N. meningitidis serogroup such as A, C, W135, Y, X or B. A useful combination of N. meningitidis protein antigens includes including one, two or three of a NHBA, a fHbp, and/or a NadA immunogen e.g. the mixture disclosed in reference 74.

Streptococcus pneumoniae: Streptococcus pneumoniae antigens include, but are not limited to, a saccharide (including a polysaccharide or an oligosaccharide) and/or protein from Streptococcus pneumoniae. The saccharide may be a polysaccharide having the size that arises during purification of the saccharide from bacteria, or it may be an oligosaccharide achieved by fragmentation of such a polysaccharide. In the 7-valent PREVNAR™ product, for instance, 6 of the saccharides are presented as intact polysaccharides while one (the 18C serotype) is presented as an oligosaccharide. In certain embodiments saccharide antigens are selected from one or more of the following pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F. An immunogenic composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. In certain embodiments, protein antigens may be selected from a protein identified in WO98/18931, WO98/18930, U.S. Pat. No. 6,699,703, U.S. Pat. No. 6,800,744, WO97/43303, WO97/37026, WO 02/079241, WO 02/34773, WO 00/06737, WO 00/06738, WO 00/58475, WO 2003/082183, WO 00/37105, WO 02/22167, WO 02/22168, WO 2003/104272, WO 02/08426, WO 01/12219, WO 99/53940, WO 01/81380, WO 2004/092209, WO 00/76540, WO 2007/116322, LeMieux et al., Infect. Imm. (2006) 74:2453-2456, Hoskins et al., J. Bacteriol. (2001) 183: 5709-5717, Adamou et al., Infect. Immun. (2001) 69(2):949-958, Briles et al., J. Infect. Dis. (2000) 182:1694-1701, Talkington et al., Microb. Pathog. (1996) 21(1):17-22, Bethe et al., FEMS Microbiol. Lett. (2001) 205(1):99-104, Brown et al., Infect. Immun. (2001) 69:6702-6706, Whalen et al., FEMS Immunol Med. Microbiol. (2005) 43:73-80, Jomaa et al., Vaccine (2006) 24(24):5133-5139. In other embodiments, *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, SpIO1, Sp130, Sp125, Sp133, pneumococcal pilus subunits.

*Streptococcus pyogenes* (Group A *Streptococcus*): Group A *Streptococcus* antigens include, but are not limited to, a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA).

*Moraxella catarrhalis*: *Moraxella* antigens include, but are not limited to, antigens identified in WO 02/18595 and WO 99/58562, outer membrane protein antigens (HMW-OMP), C-antigen, and/or LPS.

*Bordetella pertussis*: Pertussis antigens include, but are not limited to, pertussis toxoid (PT) and filamentous haemagglutinin (FHA) from *B. pertussis*, optionally also combination with pertactin and/or agglutinogens 2 and 3.

*Burkholderia*: *Burkholderia* antigens include, but are not limited to *Burkholderia mallei*, *Burkholderia pseudomallei* and *Burkholderia cepacia*.

*Staphylococcus aureus*: Staph aureus antigens include, but are not limited to, a polysaccharide and/or protein from *S. aureus*. *S. aureus* polysaccharides include, but are not limited to, type 5 and type 8 capsular polysaccharides (CP5 and CP8) optionally conjugated to nontoxic recombinant *Pseudomonas aeruginosa* exotoxin A, such as StaphVAX™, type 336 polysaccharides (336PS), polysaccharide intercellular adhesions (PIA, also known as PNAG). *S. aureus* proteins include, but are not limited to, antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, *S. aureus* antigens may be selected from a protein identified in WO 02/094868, WO 2008/019162, WO 02/059148, WO 02/102829, WO 03/011899, WO 2005/079315, WO 02/077183, WO 99/27109, WO 01/70955, WO 00/12689, WO 00/12131, WO 2006/032475, WO 2006/032472, WO 2006/032500, WO 2007/113222, WO 2007/113223, WO 2007/113224. In other embodiments, *S. aureus* antigens may be selected from IsdA, IsdB, IsdC, SdrC, SdrD, SdrE, ClfA, ClfB, SasF, SasD, SasH (AdsA), Spa, EsaC, EsxA, EsxB, Emp, H1aH35L, CP5, CP8, PNAG, 336PS.

*Staphylococcus epidermis*: *S. epidermidis* antigens include, but are not limited to, slime-associated antigen (SAA).

*Clostridium tetani* (Tetanus): Tetanus antigens include, but are not limited to, tetanus toxoid (TT). In certain embodiments such antigens are used as a carrier protein in conjunction/conjugated with the immunogenic compositions provided herein.

*Clostridium perfringens*: Antigens include, but are not limited to, Epsilon toxin from *Clostridium perfringen*.

*Clostridium botulinums* (Botulism): Botulism antigens include, but are not limited to, those derived from *C. botulinum*.

*Cornynebacterium diphtheriae* (Diphtheria): Diphtheria antigens include, but are not limited to, diphtheria toxin, preferably detoxified, such as CRM197. Additionally antigens capable of modulating, inhibiting or associated with ADP ribosylation are contemplated for combination/co-administration/conjugation with the immunogenic compositions provided herein. In certain embodiments, the diphtheria toxoids are used as carrier proteins.

*Haemophilus influenzae* B (Hib): Hib antigens include, but are not limited to, a Hib saccharide antigen. The Hib antigens may be conjugated.

*Pseudomonas aeruginosa*: *Pseudomonas* antigens include, but are not limited to, endotoxin A, Wzz protein, *P. aeruginosa* LPS, LPS isolated from PAO1 (O5 serotype), and/or Outer Membrane Proteins, including Outer Membrane Proteins F (OprF).

*Brucella*. Bacterial antigens derived from *Brucella*, including but not limited to, *B. abortus*, *B. canis*, *B. melitensis*, *B. neotomae*, *B. ovis*, *B. suis* and *B. pinnipediae*.

*Francisella*. Bacterial antigens derived from *Francisella*, including but not limited to, *F. novicida*, *F. philomiragia* and *F. tularensis*.

*Streptococcus agalactiae* (Group B *Streptococcus*): Group B *Streptococcus* antigens include, but are not limited to, a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neisserria gonorrhoeae*: Gonorrhoeae antigens include, but are not limited to, Por (or porin) protein, such as PorB (see Zhu et al., Vaccine (2004) 22:660-669), a transferring binding protein, such as TbpA and TbpB (See Price et al., Infection and Immunity (2004) 71(1): 277-283), a opacity protein (such as Opa), a reduction-modifiable protein (Rmp), and outer membrane vesicle (OMV) preparations (see Plante et al, J Infectious Disease (2000) 182:848-855), also see, e.g., WO99/24578, WO99/36544, WO99/57280, WO02/079243).

*Chlamydia trachomatis*: *Chlamydia trachomatis* antigens include, but are not limited to, antigens derived from serotypes A, B, Ba and C (agents of trachoma, a cause of blindness), serotypes L1, L2 & L3 (associated with Lymphogranuloma venereum), and serotypes, D-K. In certain embodiments, *chlamydia* trachomas antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include, but are not limited to, TmpA antigen.

*Haemophilus ducreyi* (causing chancroid): *Ducreyi* antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

Helicobacter pylori: *H pylori* antigens include, but are not limited to, CagA, VacA, NAP, HopX, HopY and/or urease antigen.

*Staphylococcus saprophyticus*: Antigens include, but are not limited to, the 160 kDa hemagglutinin of *S. saprophyticus* antigen.

*Yersinia enterocolitica* Antigens include, but are not limited to, LPS.

*E. coli*: *E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC antigens include, but are not limited to, accessory colonization factor (orf3526), orf353, bacterial Ig-like domain (group 1) protein (orf405), orf1364, NodT-family outer-membrane-factor-lipoprotein efflux transporter (orf1767), gspK (orf3515), gspJ (orf3516), tonB-dependent siderophore receptor (orf3597), fimbrial protein (orf3613), upec-948, upec-1232, A chain precursor of the type-1 fimbrial protein (upec-1875), yap H homolog (upec-2820), and hemolysin A (recp-3768).

*Bacillus anthracis* (anthrax): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but are not limited to, F1 capsular antigen, LPS, *Yersinia pestis* V antigen.

*Mycobacterium tuberculosis*: Tuberculosis antigens include, but are not limited to, lipoproteins, LPS, BCG antigens, a fusion protein of antigen 85B (Ag85B), ESAT-6 optionally formulated in cationic lipid vesicles, *Mycobacterium tuberculosis* (Mtb) isocitrate dehydrogenase associated antigens, and MPT51 antigens.

*Rickettsia*: Antigens include, but are not limited to, outer membrane proteins, including the outer membrane protein A and/or B (OmpB), LPS, and surface protein antigen (SPA).

*Listeria monocytogenes*: Bacterial antigens include, but are not limited to, those derived from *Listeria monocytogenes*.

*Chlamydia pneumoniae*: Antigens include, but are not limited to, those identified in WO 02/02606.

*Vibrio cholerae*: Antigens include, but are not limited to, proteinase antigens, LPS, particularly lipopolysaccharides of *Vibrio cholerae* II, O1 Inaba O-specific polysaccharides, *V. cholera* O139, antigens of IEM108 vaccine and Zonula occludens toxin (Zot).

*Salmonella typhi* (typhoid fever): Antigens include, but are not limited to, capsular polysaccharides preferably conjugates (Vi, i.e. vax-TyVi).

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, VlsE Antigenic Variation Protein).

*Porphyromonas gingivalis*: Antigens include, but are not limited to, *P. gingivalis* outer membrane protein (OMP).

*Klebsiella*: Antigens include, but are not limited to, an OMP, including OMP A, or a polysaccharide optionally conjugated to tetanus toxoid.

Other bacterial antigens used in the immunogenic compositions provided herein include, but are not limited to, capsular antigens, polysaccharide antigens, protein antigens or polynucleotide antigens of any of the above. Other bacterial antigens used in the immunogenic compositions provided herein include, but are not limited to, an outer membrane vesicle (OMV) preparation. Additionally, other bacterial antigens used in the immunogenic compositions provided herein include, but are not limited to, live, attenuated, and/or purified versions of any of the aforementioned bacteria. In certain embodiments, the bacterial antigens used in the immunogenic compositions provided herein are derived from gram-negative bacteria, while in other embodiments they are derived from gram-positive bacteria. In certain embodiments, the bacterial antigens used in the immunogenic compositions provided herein are derived from aerobic bacteria, while in other embodiments they are derived from anaerobic bacteria.

In certain embodiments, any of the above bacterial-derived saccharides (polysaccharides, LPS, LOS or oligosaccharides) are conjugated to another agent or antigen, such as a carrier protein (for example $CRM_{197}$). In certain embodiments, such conjugations are direct conjugations effected by reductive amination of carbonyl moieties on the saccharide to amino groups on the protein. In other embodiments, the saccharides are conjugated through a linker, such as, with succinamide or other linkages provided in *Bioconjugate Techniques*, 1996 and *CRC, Chemistry of Protein Conjugation and Cross-Linking*, 1993.

Fungal Antigens

Fungal antigens for use in the immunogenic compositions provided herein include, but are not limited to, those derived from one or more of the fungi set forth below.

Fungal antigens are derived from Dermatophytes, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*; and Fungal pathogens are derived from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale,*

*Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In certain embodiments, the process for producing a fungal antigen includes a method wherein a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

For example, the immunogen may elicit an immune response against a *Candida* fungus such as *C. albicans*. For instance, the immunogen may be a β-glucan, which may be conjugated to a carrier protein. The glucan may include β-1,3 and/or β-1,6 linkages. Suitable immunogens include those disclosed in references 75 & 76.STD Antigens In certain embodiments, the immunogenic compositions provided herein include one or more antigens derived from a sexually transmitted disease (STD). In certain embodiments, such antigens provide for prophylactic for STD's such as *chlamydia*, genital herpes, hepatitis (such as HCV), genital warts, gonorrhea, syphilis and/or chancroid. In other embodiments, such antigens provide for therapy for STD's such as *chlamydia*, genital herpes, hepatitis (such as HCV), genital warts, gonorrhea, syphilis and/or chancroid. Such antigens are derived from one or more viral or bacterial STD's. In certain embodiments, the viral STD antigens are derived from HIV, herpes simplex virus (HSV-1 and HSV-2), human papillomavirus (HPV), and hepatitis (HCV). In certain embodiments, the bacterial STD antigens are derived from *Neiserria gonorrhoeae, Chlamydia trachomatis, Treponema pallidum, Haemophilus ducreyi, E. coli,* and *Streptococcus agalactiae*. Examples of specific antigens derived from these pathogens are described above.

Respiratory Antigens

In certain embodiments, the immunogenic compositions provided herein include one or more antigens derived from a pathogen which causes respiratory disease. By way of example only, such respiratory antigens are derived from a respiratory virus such as Orthomyxoviruses (influenza), Pneumovirus (RSV), Paramyxovirus (NV), Morbillivirus (measles), Togavirus (Rubella), VZV, and Coronavirus (SARS). In certain embodiments, the respiratory antigens are derived from a bacteria which causes respiratory disease, such as, by way of example only, *Streptococcus pneumoniae, Pseudomonas aeruginosa, Bordetella pertussis, Mycobacterium tuberculosis, Mycoplasma pneumoniae, Chlamydia pneumoniae, Bacillus anthracia,* and *Moraxella catarrhalis*. Examples of specific antigens derived from these pathogens are described above.

Pediatric Vaccine Antigens

In certain embodiments, the immunogenic compositions provided herein include one or more antigens suitable for use in pediatric subjects. Pediatric subjects are typically less than about 3 years old, or less than about 2 years old, or less than about 1 years old. Pediatric antigens are administered multiple times over the course of 6 months, 1, 2 or 3 years. Pediatric antigens are derived from a virus which may target pediatric populations and/or a virus from which pediatric populations are susceptible to infection. Pediatric viral antigens include, but are not limited to, antigens derived from one or more of influenza, Mumps, measles, Rubella, polio and HBV. Paediatric bacterial antigens include antigens derived from one or more of *Streptococcus pneumoniae, Neisseria meningitidis, Bordetella pertussis, Clostridium tetani* (Tetanus), *Corynebacterium diphtheriae* (Diphtheria) and *Haemophilus influenzae* B (Hib). Examples of specific antigens derived from these pathogens are described above.

Antigens Suitable for Use in Elderly or Immunocompromised Individuals

In certain embodiments, the immunogenic compositions provided herein include one or more antigens suitable for use in elderly or immunocompromised individuals. Such individuals may need to be vaccinated more frequently, with higher doses or with adjuvanted formulations to improve their immune response to the targeted antigens. Antigens which are targeted for use in Elderly or Immunocompromised individuals include antigens derived from one or more of the following pathogens: *Neisseria meningitidis, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Corynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Chlamydia pneumoniae,* Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

Antigens Suitable for Use in Adolescent Vaccines

In certain embodiments, the immunogenic compositions provided herein include one or more antigens suitable for use in adolescent subjects. Adolescents are in need of a boost of a previously administered pediatric antigen. Pediatric antigens which are suitable for use in adolescents are described above. In addition, adolescents are targeted to receive antigens derived from an STD pathogen in order to ensure protective or therapeutic immunity before the beginning of sexual activity. STD antigens which are suitable for use in adolescents are described above.

Tumor Antigens

In certain embodiments, a tumor antigen or cancer antigen is used in conjunction with the immunogenic compositions provided herein. In certain embodiments, the tumor antigens is a peptide-containing tumor antigens, such as a polypeptide tumor antigen or glycoprotein tumor antigens. In certain embodiments, the tumor antigen is a saccharide-containing tumor antigen, such as a glycolipid tumor antigen or a ganglioside tumor antigen. In certain embodiments, the tumor antigen is a polynucleotide-containing tumor antigen that expresses a polypeptide-containing tumor antigen, for instance, an RNA vector construct or a DNA vector construct, such as plasmid DNA.

Tumor antigens appropriate for the use in conjunction with the immunogenic compositions provided herein encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

In certain embodiments, the tumor antigens are, for example, (a) full length molecules associated with cancer cells, (b) homologs and modified forms of the same, including molecules with deleted, added and/or substituted portions, and (c) fragments of the same. In certain embodiments, the tumor antigens are provided in recombinant form. In certain embodiments, the tumor antigens include, for example, class I-restricted antigens recognized by CD8+ lymphocytes or class II-restricted antigens recognized by CD4+ lymphocytes.

In certain embodiments, the tumor antigens include, but are not limited to, (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins are coupled to a carrier protein (e.g., MUC-1 are coupled to KLH); (ii) lipopolypeptides (e.g., MUC-1 linked to a lipid moiety); (iii) polysaccharides (e.g., Globo H synthetic hexasaccharide), which are coupled to a carrier proteins (e.g., to KLH), (iv) gangliosides such as GM2, GM12, GD2, GD3 (associated with, e.g., brain, lung cancer, melanoma), which also are coupled to carrier proteins (e.g., KLH).

In certain embodiments, the tumor antigens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

Polynucleotide-containing antigens used in conjunction with the immunogenic compositions provided herein include polynucleotides that encode polypeptide cancer antigens such as those listed above. In certain embodiments, the polynucleotide-containing antigens include, but are not limited to, DNA or RNA vector constructs, such as plasmid vectors (e.g., pCMV), which are capable of expressing polypeptide cancer antigens in vivo.

In certain embodiments, the tumor antigens are derived from mutated or altered cellular components. After alteration, the cellular components no longer perform their regulatory functions, and hence the cell may experience uncontrolled growth. Representative examples of altered cellular components include, but are not limited to ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor.

Various other immunogens may be used.

Carrier Moieties

Saccharide antigens may be conjugated to a carrier moiety.

The carrier moiety may be a protein. Typical carrier proteins are bacterial toxins, such as diphtheria or tetanus toxins, or toxoids or mutants or fragments thereof. The CRM197 diphtheria toxin mutant [77] is useful. Other suitable carrier proteins include the *N. meningitidis* outer membrane protein complex [78], synthetic peptides [79,80], heat shock proteins [81,82], pertussis proteins [83,84], cytokines [85], lymphokines [85], hormones [85], growth factors [85], artificial proteins comprising multiple human CD4$^+$ T cell epitopes from various pathogen-derived antigens [86] such as N19 [87], protein D from *H. influenzae* [88-90], pneumolysin [91] or its non-toxic derivatives [92], pneumococcal surface protein PspA [93], iron-uptake proteins [94], toxin A or B from *C. difficile* [95], recombinant *P. aeruginosa* exoprotein A (rEPA) [96], etc. In some embodiments the carrier protein is a *S. aureus* protein, such as an antigen selected from the first, second, third or fourth antigen groups.

Where a composition includes more than one immunogen, each immunogen may use the same carrier protein or a different carrier protein.

Conjugates may have excess carrier (w/w) or excess antigen (w/w). In some embodiments, a conjugate may include substantially equal weights of each.

The carrier molecule may be covalently conjugated to the carrier directly or via a linker. Direct linkages to the protein may be achieved by, for instance, reductive amination between the antigen and the carrier, as described in, for example, references 97 and 98. The antigen may first need to be activated e.g. by oxidation. Linkages via a linker group may be made using any known procedure, for example, the procedures described in references 99 and 100. A preferred type of linkage is an adipic acid linker, which may be formed by coupling a free —$NH_2$ group (e.g. introduced to a glucan by amination) with adipic acid (using, for example, diimide activation), and then coupling a protein to the resulting antigen-adipic acid intermediate [101,102]. Another preferred type of linkage is a carbonyl linker, which may be formed by reaction of a free hydroxyl group of a saccharide CDI [103, 104] followed by reaction with a protein to form a carbamate linkage. Other linkers include β-propionamido [105], nitrophenyl-ethylamine[106], haloacyl halides [107], glycosidic linkages [108], 6-aminocaproic acid [109], ADH [110], $C_4$ to $C_{12}$ moieties [111], etc. Carbodiimide condensation can also be used [112].

Further Non-Active Components

Compositions of the invention can include components in addition to the immunogen, TLR agonist, and needle material e.g. they typically include one or more pharmaceutical carrier(s) and/or excipient(s). A thorough discussion of such components is available in reference 113. These components may be added to facilitate the solid nature of the composition, or may be residual from the earlier aqueous nature of a component.

Compositions may include one or more preservatives, such as thiomersal or 2-phenoxyethanol. Mercury-free compositions are preferred, and preservative-free vaccines can be prepared.

Compositions can include a physiological salt, such as a sodium salt. Sodium chloride (NaCl) is typical, which may be present at between 1 and 20 mg/ml e.g. 10±2 mg/ml or 9 mg/ml. Other salts that may be present include potassium chloride, potassium dihydrogen phosphate, disodium phosphate dehydrate, magnesium chloride, calcium chloride, etc. Compositions used for intradermal delivery preferably do not include aluminium salts such as aluminium phosphate and aluminium hydroxide.

Compositions may include one or more buffer salts. Buffering salts may be added to provide buffering when the composition is redissolved. Typical buffers include: a phosphate buffer; a Tris buffer; a borate buffer; a succinate buffer; a histidine buffer; or a citrate buffer. Buffer salt s will typically be included in the 5-20 mM range. If a phosphate buffer is used then the concentration of phosphate ions should, in some embodiments, be <50 mM (see above) e.g. <10 mM.

Compositions typically have a pH between 5.0 and 9.5 e.g. between 6.0 and 8.0. The pH of solid compositions is the pH of the composition when re-dissolved in water.

Compositions are preferably sterile, non-pyrogenic (e.g. containing <1 EU (endotoxin unit, a standard measure) per dose, and preferably <0.1 EU per dose), and/or gluten-free.

Compositions are suitable for administration to animal (and, in particular, human) patients, and thus include both human and veterinary uses. They may be used in a method of raising an immune response in a patient, comprising the step of administering the composition to the patient. Compositions may be administered before a subject is exposed to a pathogen and/or after a subject is exposed to a pathogen. A composition is administered by applying it to the skin of a subject.

The invention also provides a hermetically sealed container containing a composition of the invention. Suitable containers include e.g. a pouch or envelope.

Dosing

The total dose of immunogen in a skin patch may be 10 μg/patch-100 μg/patch. The total dose may be 10, 15, 20, 25, 30, 35, 40, 45, 50, 55, 60, 65, 70, 75, 80, 85, 90, 95 or 100 μg/patch. The particular dose used is dependent on the particular immunogen and the particular TLR agonist used. Intradermal administration may allow lower doses of immunogen and TLR agonist to be used in comparison to those required for intramuscular administration.

The total dose of TLR agonist provided in a skin patch may be 10 μg/patch-100 μg/patch. The total dose may be 10, 15, 20, 25, 30, 35, 40, 45, 50, 55, 60, 65, 70, 75, 80, 85, 90, 95 or 100 μg/patch. The particular dose used is dependent on the particular immunogen and the particular TLR agonist used. Intradermal administration may allow lower doses of immunogen and TLR agonist to be used in comparison to those required for intramuscular administration.

The ratio of antigen to TLR agonist (by mass) may be around 10:1.

Immunogen Concentration

Immunogenic compositions delivered intradermally by microneedles may require much lower volumes than the typical immunogenic compositions delivered intramuscularly, but they may require the same amount of antigen, which will often require a more concentrated bulk antigen.

Various techniques can be used for this concentration step including, but not limited to: centrifugal filtration; ultrafiltration; or tangential flow filtration (also known as crossflow filtration).

Centrifugal filtration involves centrifugation of a liquid through a filter. The filter retains the antigen to be concentrated but does not retain solvent or smaller solutes. As the volume of the filtrate increases, the concentration of the antigen in the retentate also increases. This technique typically uses a fixed angle rotor. Various suitable centrifugal filtration devices are commercially available e.g. the products sold under trade marks Centricon™, Vivaspin™ and Spintek™. The cut-off of the filter will be selected such that the antigen of interest remains in the retentate.

Ultrafiltration involves the use of hydrostatic pressure to force a liquid against a semipermeable membrane. The filter retains the antigen to be concentrated but does not retain solvent or smaller solutes. Continued application of hydrostatic pressure causes the volume of the filtrate to increase, and thus the concentration of the antigen in the retentate also increases. Many ultrafiltration membranes are commercially available. The molecular weight cut-off (MWCO) of an ultrafiltration membrane determines which solutes can pass through the membrane (i.e. into the filtrate) and which are retained (i.e. in the retentate). The MWCO of the filter used with the invention will be selected such that substantially all of the antigen of interest remains in the retentate.

Tangential flow filtration (TFF) involves passing a liquid tangentially across a filter membrane. The sample side is typically held at a positive pressure relative to the filtrate side. As the liquid flows over the filter, components therein can pass through the membrane into the filtrate. Continued flow causes the volume of the filtrate to increase, and thus the concentration of the antigen in the retentate increases. TFF contrasts with deadend filtration, in which sample is passed through a membrane rather than tangentially to it. Many TFF systems are commercially available. The MWCO of a TFF membrane determines which solutes can pass through the membrane (i.e. into the filtrate) and which are retained (i.e. in the retentate). The MWCO of a TFF filter used with the invention will be selected such that substantially all of the antigen of interest remains in the retentate.

These three concentration techniques are not mutually exclusive.

Whichever technique is chosen, it preferably increases the concentration of the antigen of interest by at least n-fold relative to the initial concentration, where n is 5, 6, 7, 8, 9, 10, 12, 15, 20, 25, 30, 35, 40, 45, 50, 60, 70, 80 or more.

Lyophilisation

Following antigen concentration, a lyophilisation step may be used.

Lyophilisation typically involves three stages within a chamber: (a) freezing; (b) primary drying; and (c) secondary drying. Step (a) freezes the mobile water of the conjugate. In step (b) the chamber pressure is reduced (e.g. to ≤0.1 Torr) and heat is applied to the product to cause the frozen water to sublime. In step (c) the temperature is increased to desorb any bound water, such as water of crystallisation, until the residual water content falls to the desired level.

An initial step in a typical lyophilisation, before freezing occurs, is addition of a lyoprotectant. In some embodiments a lyoprotectant may have been added prior to concentration in step (i), but it is preferred to add it instead after concentration has occurred i.e. at the end of step (i) or at the start of step (ii). This makes it easier to control the amount of lyoprotectant which is present at the start of lyophilisation freezing.

Thus a one or more lyoprotectants may be added to the concentrated antigen. Suitable lyoprotectants include, but are not limited to, sugar alcohols (such as sorbitol, mannitol, maltitol, erythritol, xylitol) and disaccharides (such as sucrose, trehalose, maltose, lactulose, lactose, cellobiose). Sucrose and mannitol (or a mixture thereof) are preferred lyoprotectants for use with the invention.

After lyophilisation, a lyophilised vaccine antigen can be reconstituted. This reconstitution can use water (e.g. water for injection, wfi) or buffer (e.g. a phosphate buffer, a Tris buffer, a borate buffer, a succinate buffer, a histidine buffer, or a citrate buffer). Buffers will typically be included in the 5-20 mM range. A phosphate buffer is preferred.

Step (i) concentrated the first liquid volume of vaccine antigen, providing a composition with the same amount of antigen in a second (reduced) liquid volume. Step (ii) dried this concentrated material. This dried material can be reconstituted in a third liquid volume. If the third volume is greater than the first volume, the overall process has failed to concentrate the antigen. Similarly, if the third volume is greater than the second volume, the reconstitution step has gone backwards in terms of concentration. Thus the third volume is either equal to or, preferably, less than the second volume. Thus the lyophilisation/reconstitution steps can achieve a further antigen concentration.

The TLR agonist may be added to the immunogenic composition following antigen concentration.

Methods of Treatment, and Administration of Immunogenic Compositions

The invention provides a method of raising an immune response in a subject, comprising the step of intradermally administering to the subject a TLR agonist and an immunogen.

The invention also provides a composition comprising a TLR agonist and an immunogen, for use in a method of raising an immune response in a subject by intradermal delivery.

The invention also provides the use of a TLR agonist and an immunogen in the manufacture of a intradermal medicament for raising an immune response in a subject. Further details of the medicament are provided above.

The invention is suitable for raising immune responses in human or non-human animal (in particular mammal) subjects. Compositions prepared according to the invention may be used to treat both children and adults.

The immune response stimulated by these methods and uses will generally include an antibody response, preferably a protective antibody response. Methods for assessing antibody responses after immunisation are well known in the art.

Chemical Groups

Unless specifically defined elsewhere, the chemical groups discussed herein have the following meaning when used in present specification:

The term "alkyl" includes saturated hydrocarbon residues including:

linear groups up to 10 atoms ($C_1$-$C_{10}$), or of up to 6 atoms ($C_1$-$C_6$), or of up to 4 atoms ($C_1$-$C_4$). Examples of such alkyl groups include, but are not limited, to $C_1$-methyl, $C_2$-ethyl, $C_3$-propyl and $C_4$-n-butyl.

branched groups of between 3 and 10 atoms ($C_3$-$C_{10}$), or of up to 7 atoms ($C_3$-$C_7$), or of up to 4 atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.

The term "alkylene" refers to the divalent hydrocarbon radical derived from an alkyl group, and shall be construed in accordance with the definition above.

The term "alkenyl" includes monounsaturated hydrocarbon residues including:

linear groups of between 2 and 6 atoms ($C_2$-$C_6$). Examples of such alkenyl groups include, but are not limited to, $C_2$-vinyl, $C_3$-1-propenyl, $C_3$-allyl, $C_4$-2-butenyl branched groups of between 3 and 8 atoms ($C_3$-$C_8$). Examples of such alkenyl groups include, but are not limited to, $C_4$-2-methyl-2-propenyl and $C_6$-2,3-dimethyl-2-butenyl.

The term alkenylene refers to the divalent hydrocarbon radical derived from an alkenyl group, and shall be construed in accordance with the definition above.

The term "alkoxy" includes O-linked hydrocarbon residues including:

linear groups of between 1 and 6 atoms ($C_1$-$C_6$), or of between 1 and 4 atoms ($C_1$-$C_4$). Examples of such alkoxy groups include, but are not limited to, $C_1$-methoxy, $C_2$-ethoxy, $C_3$-n-propoxy and $C_4$-n-butoxy.

branched groups of between 3 and 6 atoms ($C_3$-$C_6$) or of between 3 and 4 atoms ($C_3$-$C_4$). Examples of such alkoxy groups include, but are not limited to, $C_3$-iso-propoxy, and $C_4$-sec-butoxy and tert-butoxy.

Halo is selected from Cl, F, Br and I. Halo is preferably F.

The term "aryl" includes a single or fused aromatic ring system containing 6 or 10 carbon atoms; wherein, unless otherwise stated, each occurrence of aryl may be optionally substituted with up to 5 substituents independently selected from ($C_1$-$C_6$)alkyl, ($C_1$-$C_6$)alkoxy, OH, halo, CN, COOR$^{14}$, CF$_3$ and NR$^{14}$R$^{15}$; as defined above. Typically, aryl will be optionally substituted with 1, 2 or 3 substituents. Optional substituents are selected from those stated above. Examples of suitable aryl groups include phenyl and naphthyl (each optionally substituted as stated above). Arylene refers the divalent radical derived from an aryl group, and shall be construed in accordance with the definition above.

The term "heteroaryl" includes a 5, 6, 9 or 10 membered mono- or bi-cyclic aromatic ring, containing 1 or 2 N atoms and, optionally, an $NR^{14}$ atom, or one $NR^{14}$ atom and an S or an O atom, or one S atom, or one O atom; wherein, unless otherwise stated, said heteroaryl may be optionally substituted with 1, 2 or 3 substituents independently selected from $(C_1$-$C_6)$alkyl, $(C_1$-$C_6)$alkoxy, OH, halo, CN, $COOR^{14}$, $CF_3$ and $NR^{14}R^{15}$; as defined below. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above). Heteroarylene refers the divalent radical derived from heteroaryl, and shall be construed in accordance with the definition above.

The term "heterocyclyl" is a C-linked or N-linked 3 to 10 membered non-aromatic, mono- or bi-cyclic ring, wherein said heterocycloalkyl ring contains, where possible, 1, 2 or 3 heteroatoms independently selected from N, $NR^{14}$, $S(O)_q$ and O; and said heterocycloalkyl ring optionally contains, where possible, 1 or 2 double bonds, and is optionally substituted on carbon with 1 or 2 substituents independently selected from $(C_1$-$C_6)$alkyl, $(C_1$-$C_6)$alkoxy, OH, CN, $CF_3$, halo, $COOR^{14}$, $NR^{14}R^{15}$ and aryl.

In the above definitions $R^{14}$ and $R^{15}$ are independently selected from H and $(C_1$-$C_6)$alkyl.

When a structural formula is defined with a substituent attached to the core of the molecule by an unspecified, or "floating" bond, this definition encompasses the cases where the unspecified substituent is attached to any of the atoms on the ring in which the floating bond is located, whilst complying with the allowable valence for that atom.

In the case of compounds of the invention which may exist in tautomeric forms (i.e. in keto or enol forms), reference to a particular compound optionally includes all such tautomeric forms.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated otherwise, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Intradermal Delivery of Immunogenic Compositions
Influenza

Immunization of Balb/c mice with 100 µl or 20 µl immunogenic composition was carried out using both intramuscular delivery and intradermal delivery. The composition included a trivalent influenza vaccine with a 1 µg HA dose of each of X181 H1N1 Cal, X187 H3N2 Perth and B/Brisbane and one of a group of adjuvants including TLR agonists. Mice were anaesthetized before immunization. For the mice receiving intradermal immunization, an area on the back of the mouse was shaved or plucked to remove the hair at the injection site. The site was swabbed with 70% ethanol. The needle was inserted, bevel up, with the needle held nearly parallel to the plane of the skin. Both the mice receiving intramuscular and intradermal immunization, a number of different TLR agonists were used and the doses administrated, the total volume of the composition used and the route of administration are shown in Table 1 below. Using volumes of 50 µl or less per site for intradermal delivery avoids tissue trauma.

TABLE 1

| Group | Adjuvant | Dose | Total volume | Route |
|---|---|---|---|---|
| 1 | — | — | 100 ul | IM |
| 2 | MF59 | (1:1) | 100 µl | IM |
| 3 | — | — | 100 µl | IM |
| 4 | — | — | 20 µl | ID |
| 5 | T1a | 50 µg | 20 µl | ID |
| 6 | T1b | 50 µg | 20 µl | ID |
| 7 | T1b | 100 µg | 20 µl | ID |
| 8 | T2 | 50 µg | 20 µl | ID |
| 9 | LTK63 | 5 µg | 20 µl | ID |
| 10 | α-GalCer | 5 µg | 20 µl | ID |
| 11 | MPLA | 25 µg | 20 µl | ID |
| 12 | MF59 | (1:1) | 20 µl | ID |

The T1a adjuvant was formulated by dispersion in 0.05% carboxymethyl cellulose or 0.05% Tween80 and sonicated in a water bath. The T1b adjuvant was formulated by dispersion in 1x and sonicated in a water bath. The T2 adjuvant was formulated by dispersion in 10 mM ammonia solution and sonicated in a water bath. The LTK63 adjuvant [114] was formulated in 0.05M sodium phosphate and 0.2M L-arginine. The α-GalCer adjuvant was formulated in water and 0.05% Tween20 and sonicated in a water bath for 30 minutes at 37° C. The MPL adjuvant was formulated by aqueous dispersion using 0.5% TEoA/WFI.

Figure 1:
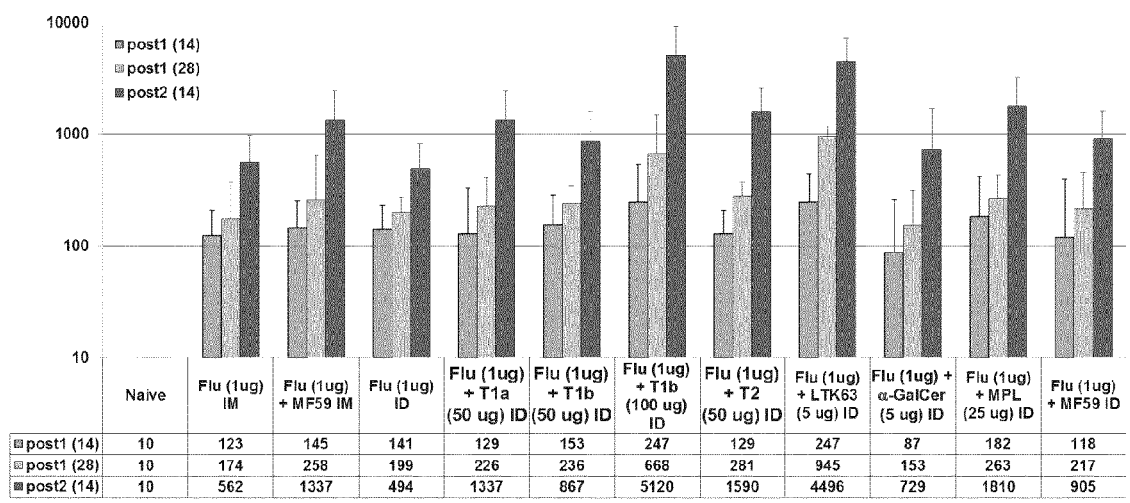
FIG. 1: anti-H1N1 hemagglutination inhibition (HI) titers provided by intradermal and intramuscular delivery of influenza antigen and TLR agonists following two immunizations.
Figure 2:
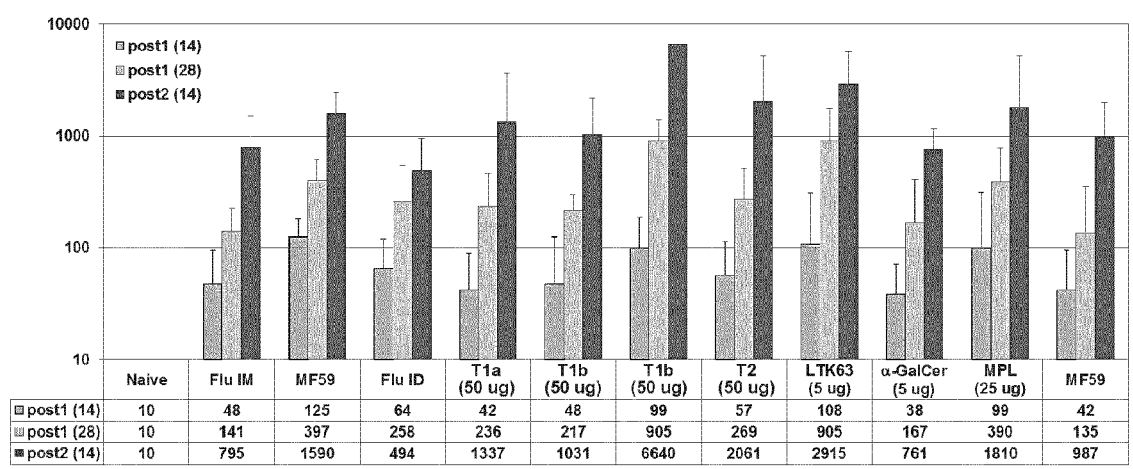
FIG. 2: anti-H3N2 HI titers provided by intrad material had a HA concentration (as measured by SRID) comparable to the starting material, indicating no loss of functional antigen. The reconstituted material was stable for >2 weeks.
Figure 3:
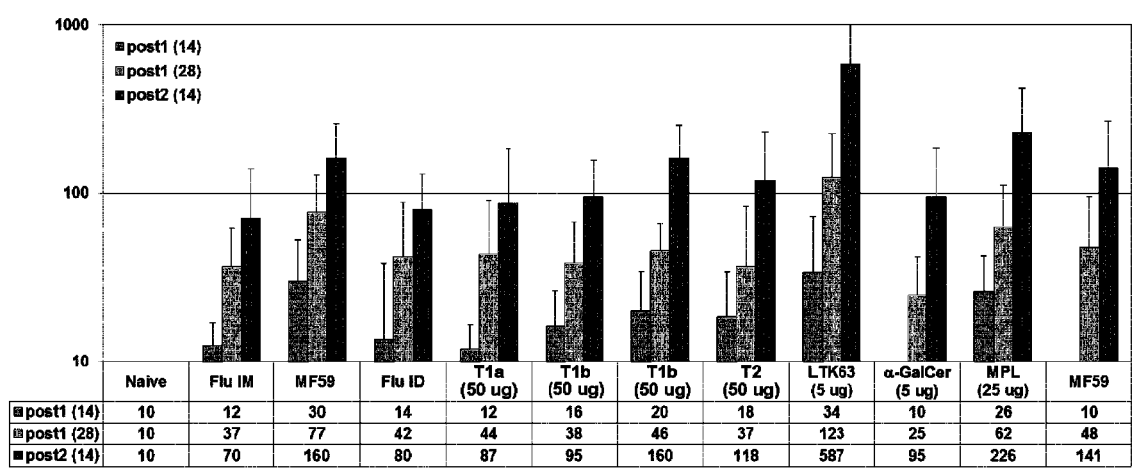

Two immunizations were carried out 28 days apart, and individual samples were analyzed for anti-H1N1, anti H3N2 and anti-B hemagglutination inhibition (HI) titers 14 and 28 days after the first immunization and 14 days after the second immunization. FIGS. 1-3 show the HI titers for anti-H1N1, anti-H3N2 and anti-B respectively.

When administered intradermally, the influenza antigens induce comparable HI titers to those induced following intramuscular administration. An improved immune response was provided following a second intradermal immunization in the presence each of the TLR agonists compared to intradermal immune in the absence of a TLR agonist. The immune response provided by intradermal immunization with antigen alone or antigen plus MF59 is comparable to the immune response provided by intramuscular immunization with antigen alone or antigen plus MF59.

Intradermal immunization with T1b (100 µg) or LTK63 (5 µg) provided a significantly improved immune response compared to both intradermal or intramuscular immunization using antigen alone.

Neisseria meningitidis

Immunization of CD1 mice with 100 µl immunogenic composition comprising a 10 µg dose of three N. meningitidis B antigens [74] and one of a group of adjuvants including TLR agonists was carried out using both intramuscular delivery and intradermal delivery. Mice were anaesthatized before immunization. An area on the back of the mouse was shaved or plucked to remove the hair at the injection site. The site was swabbed with 70% ethanol. The needle was inserted, bevel up, with the needle held nearly parallel to the plane of the skin. A number of different TLR agonists were used and the doses administrated, the total volume of the composition used and the route of administration are shown in Table 2 below.

| Group | Adjuvant | Dose | Total volume | Route |
|---|---|---|---|---|
| 1 | — | — | 100 ul | IM |
| 2 | — | — | 100 µl | ID |
| 3 | T1a | 100 µg | 100 µl | IM |
| 4 | T1a | 100 µg | 100 µl | ID |
| 5 | T1b | 100 µg | 100 µl | IM |
| 6 | T1b | 100 µg | 100 µl | ID |
| 7 | T2 | 100 µg | 100 µl | IM |
| 8 | T2 | 100 µg | 100 µl | ID |
| 9 | Alum/T1c | 100 µg | 100 µl | IM |
| 10 | Alum/T1c | 100 µg | 100 µl | ID |

The T1a adjuvant was formulated by dispersion in 0.05% carboxymethyl cellulose or 0.05% Tween80 and sonicated in a water bath. The T1b adjuvant was formulated by dispersion in 1x and sonicated in a water bath. The T2 adjuvant was formulated by dispersion in 10 mM $NH_3$ solution and sonicated in a water bath.

Figure 4:
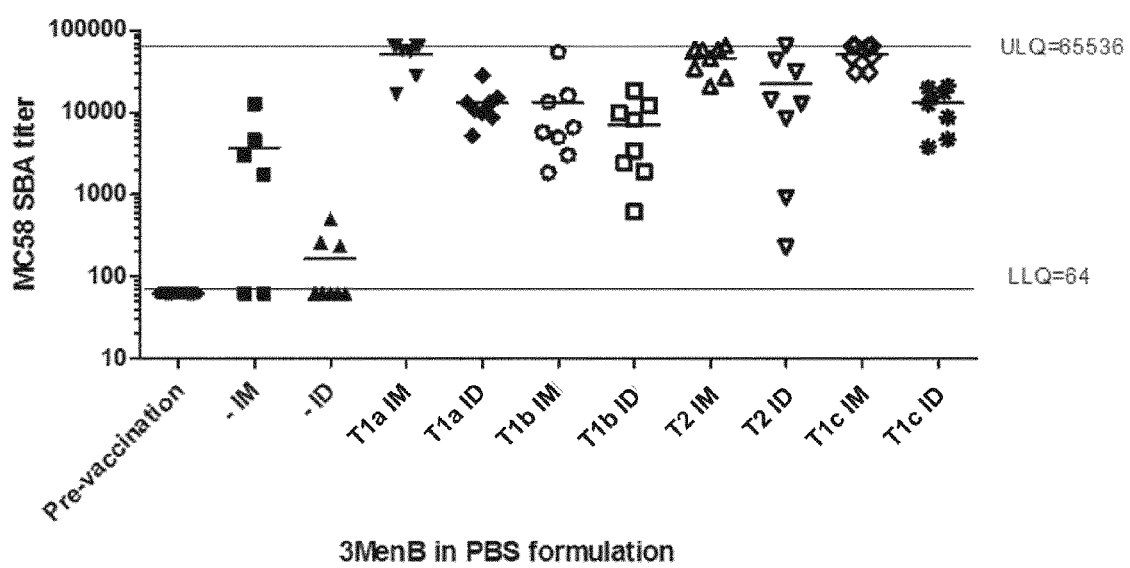

Immunizations were carried out, and individual samples were analysed for bactericidal activity. FIG. 4 shows the bactiericidal titers for each of the compositions tested.

When administered intradermally, the MenB antigens induce higher bactericidal titers to those induced following intramuscular administration even without the presence of TLR agonists. Intradermal immunization with T2 provides an improved immune response compared to combination of the antigens with other adjuvants. The immune response provided following intradermal administration of meningitidis antigens and TLR agonists is comparable to the immune response provided following intramuscular administration of meningitidis antigens and TLR agonists.

It will be understood that the invention has been described by way of example only and modifications may be made whilst remaining within the scope and spirit of the invention.

REFERENCES

[1] Prausnitz et al. (2009) Curr Top Microbiol Immunol. 333:369-93.
[2] Kang et al. (2012) Expert Rev Vaccines. 11(5):547-60.
[3] Davidson et al. (2008) Chemical Engineering Research and Design 86:1196-1206.
[4] Carey et al. (2011) PLoS ONE 6(7): e22442.
[5] Bal et al. (2010) J Control Release. 147:218-24.
[6] Donnelly et al. (2011) Pharm Res 28:41-57.
[7] Koutsonanos et al. (2009) PLoS ONE 4(e): e4773.
[8] Quan et al. (2009) PLoS ONE 4(9):e7152.
[9] Matsuo et al. (2012) J Control Release 161:10-17.

[10] US-2011/112509.
[11] WO2009/040548.
[12] Lee et al. (2008) *Biomaterials* 29(13):2113-24.
[13] WO2007/030477.
[14] U.S. Pat. No. 6,945,952.
[15] U.S. Pat. No. 7,211,062.
[16] Sullivan et al. (2010) *Nature Med* 16:915-920.
[17] US-2009/0182306
[18] U.S. Pat. No. 7,182,747.
[19] Oh et al. (2006) American Association of Pharmaceutical Scientists, 2006 Annual Meeting and Exposition. *The AAPS Journal*. 8(S2).
[20] WO2007/127976.
[21] Matsuo et al. (2012) *J Control Release*. 160(3):495-501.
[22] Koutsonanos et al. (2012) *Sci Rep*. 2:357.
[23] EP-A-2289843.
[24] Gill & Prausnitz (2007) *J Control Release* 117:227-37.
[25] WO2007/124393.
[26] WO2007/061964.
[27] WO2007/059289.
[28] Jin et al. (2009) *Biomed Microdevices*. 11(6):1195-203.
[29] Vrdoljak et al. (2012) *J Control Release* 159:34-42.
[30] Rosenberg et al. (2010) *J Immunol* 184:136.20.
[31] U.S. Pat. No. 4,666,886.
[32] WO2009/118296.
[33] WO2008/005555.
[34] WO2009/111337.
[35] WO2009/067081.
[36] WO2007/040840.
[37] WO2010/014913.
[38] WO2011/049677.
[39] WO2012/031140
[40] WO2011/119759.
[41] US2010/0143301.
[42] GB-A-2220211.
[43] Myers et al. (1990) pages 145-156 of *Cellular and molecular aspects of endotoxin reactions*.
[44] Ulrich (2000) Chapter 16 (pages 273-282)
[45] Johnson et al. (1999) *J Med Chem* 42:4640-9.
[46] Baldrick et al. (2002) *Regulatory Toxicol Pharmacol* 35:398-413.
[47] Coler et al. (2011) *PLoS ONE* 6(1):e16333.
[48] Johnson et al. (1999) *Bioorg Med Chem Lett* 9:2273-2278.
[49] Evans et al. (2003) *Expert Rev Vaccines* 2:219-229.
[50] Bazin et al. (2006) *Tetrahedron Lett* 47:2087-92.
[51] Wong et al. (2003) *J Clin Pharmacol* 43(7):735-42.
[52] US2005/0215517.
[53] WO03/011223.
[54] WO2007/053455.
[55] De Libero et al, *Nature Reviews Immunology*, 2005, 5: 485-496.
[56] U.S. Pat. No. 5,936,076.
[57] Oki et al, *J. Clin. Investig.*, 113: 1631-1640.
[58] US2005/0192248.
[59] Yang et al, *Angew. Chem. Int. Ed.*, 2004, 43: 3818-3822.
[60] WO2008/047174.
[61] WO2008/047249.
[62] WO2005/102049.
[63] Goff et al, *J. Am. Chem., Soc.*, 2004, 126: 13602-13603.
[64] WO03/105769.
[65] Peppoloni et al. (2003) *Expert Rev Vaccines* 2:285-93.
[66] WO95/17211.
[67] da Hora et al. (2011) *Vaccine* 29:1538-44.
[68] WO93/13202.
[69] Pizza et al. (2000) *Int J Med Microbiol* 290:455-61.
[70] WO98/18928.
[71] Feng et al. (2005) *Acta Biochim Biophys Sin* (Shanghai). 37(2):126-32.
[72] Treanor et al. (1996) *J Infect Dis* 173:1467-70.
[73] Keitel et al. (1996) *Clin Diagn Lab Immunol* 3:507-10.
[74] Giuliani et al. (2006) *Proc Natl Acad Sci USA*. 103: 10834-9.
[75] WO03/097091.
[76] Cassone & Torosantucci (2006) *Expert Rev Vaccines* 5:859-67.
[77] Research Disclosure, 453077 (January 2002).
[78] EP-A-0372501.
[79] EP-A-0378881.
[80] EP-A-0427347.
[81] WO93/17712.
[82] WO94/03208.
[83] WO98/58668.
[84] EP-A-0471177.
[85] WO91/01146.
[86] Falugi et al. (2001) *Eur J Immunol* 31:3816-3824.
[87] Baraldo et al. (2004) *Infect Immun* 72(8):4884-7.
[88] EP-A-0594610.
[89] Ruan et al. (1990) *J Immunol* 145:3379-3384.
[90] WO00/56360.
[91] Kuo et al. (1995) *Infect Immun* 63:2706-13.
[92] Michon et al. (1998) *Vaccine*. 16:1732-41.
[93] WO02/091998.
[94] WO01/72337.
[95] WO00/61761.
[96] WO00/33882
[97] U.S. Pat. No. 4,761,283.
[98] U.S. Pat. No. 4,356,170.
[99] U.S. Pat. No. 4,882,317.
U.S. Pat. No. 4,695,624.
*Mol. Immunol.*, 1985, 22, 907-919
EP-A-0208375.
Bethell G. S. et al., *J. Biol. Chem.*, 1979, 254, 2572-4
Hearn M. T. W., *J. Chromatogr.*, 1981, 218, 509-18
WO00/10599.
Gever et al., *Med. Microbiol. Immunol*, 165: 171-288 (1979).
U.S. Pat. No. 4,057,685.
U.S. Pat. Nos. 4,673,574; 4,761,283; 4,808,700.
U.S. Pat. No. 4,459,286.
U.S. Pat. No. 4,965,338.
U.S. Pat. No. 4,663,160.
WO2007/000343.
*Remington: The Science and Practice of Pharmacy* (Gennaro, 2000; 20th edition, ISBN: 0683306472)
Tritto et al. (2007) *J. Immunol.* 179:5346-5357.

What is claimed is:

1. An intradermal delivery system comprising a microneedle, wherein the microneedle comprises a Toll-like Receptor 7 (TLR7) agonist and a bacterial antigen or a viral antigen, wherein the TLR7 agonist is a TLR7 agonist having formula T1:

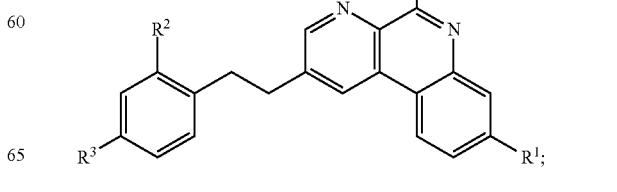

wherein $R^1$ is $C_1$-$C_6$alkyl, -$L^2R^5$, -$L^2R^6$, —$OL^2R^5$, or —$OL^2R^6$;

$R^2$ is $C_1$alkyl;

$R^3$ is selected from $C_1$-$C_4$alkyl, -$L^3R^5$, -$L^3R^7$, —$OL^3R^5$, —$OL^3R^7$, —$OR^8$, and —$C(R^5)_2OH$;

$L^2$ is $C_1$-$C_6$alkylene, or —$((CR^4R^4)_pO)_q(CH_2)_p$—, wherein the $C_1$-$C_6$alkylene of $L^2$ is optionally substituted with 1 to 4 fluoro groups;

each $L^3$ is independently selected from $C_1$-$C_6$alkylene and —$((CR^4R^4)_pO)_q(CH_2)_p$— wherein the $C_1$-$C_6$alkylene of $L^3$ is optionally substituted with 1 to 4 fluoro groups;

$R^4$ is H;

$R^5$ is —$P(O)(OR^9)_2$;

$R^6$ is —$CF_2P(O)(OR^9)_2$ or —$C(O)OR^{10}$;

$R^7$ is —$CF_2P(O)(OR^9)_2$ or —$C(O)OR^{10}$;

$R^8$ is H or $C_1$-$C_4$alkyl;

each $R^9$ is independently selected from H and $C_1$-$C_6$alkyl;

$R^{10}$ is H or $C_1$-$C_4$alkyl;

each p is independently selected from 1, 2, 3, 4, 5 and 6, and q is 1, 2, 3 or 4.

2. The intradermal delivery system of claim 1, wherein the microneedle is a hollow microneedle.

3. The intradermal delivery system of claim 1 comprising a solid biodegradable microneedle.

4. The intradermal delivery system of claim 1, wherein the microneedle is a solid microneedle.

5. A process for preparing the intradermal delivery system of claim 4, wherein the method comprises the steps of a) mixing the bacterial antigen or the viral antigen and the TLR7 agonist to form an immunogenic composition in which the immunogen has a concentration of 10 mg/ml-50 mg/ml and the TLR7 agonist has a concentration of 0.1 mg/ml-10 mg/ml and b) drying the immunogenic composition to form a solid microneedle.

* * * * *